US009278999B2

(12) United States Patent
Simonson et al.

(10) Patent No.: US 9,278,999 B2
(45) Date of Patent: Mar. 8, 2016

(54) INFLUENZA C VIRUS AND VACCINE

(75) Inventors: Randy R. Simonson, Worthington, MN (US); Benjamin M. Hause, Currie, MN (US); Emily A. Collin, Windom, MN (US)

(73) Assignee: NEWPORT LABORATORIES, Worthington, MN (US)

( * ) Notice: Subject to any disclaimer, the term of this patent is extended or adjusted under 35 U.S.C. 154(b) by 247 days.

(21) Appl. No.: 13/385,004

(22) Filed: Jan. 27, 2012

(65) Prior Publication Data

US 2013/0195915 A1 Aug. 1, 2013

(51) Int. Cl.

*A61K 39/145* (2006.01)
*C07K 14/005* (2006.01)
*C12N 7/00* (2006.01)
*A61K 39/00* (2006.01)

(52) U.S. Cl.

CPC ................ *C07K 14/005* (2013.01); *C12N 7/00* (2013.01); *A61K 2039/5252* (2013.01); *C12N 2760/16321* (2013.01); *C12N 2760/16322* (2013.01); *C12N 2760/16334* (2013.01)

(58) Field of Classification Search

None
See application file for complete search history.

(56) References Cited

U.S. PATENT DOCUMENTS

2003/0119782 A1* 6/2003 Cham ............................. 514/54
2009/0110698 A1* 4/2009 Hause et al. ............... 424/206.1

FOREIGN PATENT DOCUMENTS

WO WO 2009/040343 A1 4/2009

OTHER PUBLICATIONS

Guo et al. J gen. Virol. 1983 vol. 64, pp. 177-182.*
Hause BM et al., (2013) Isolation of a Novel Swine Influenza Virus from Oklahoma in 2011 Which Is Distantly Related to Human Influenza C Viruses. PLoS Pathog 9(2): e1003176 (no specific pages given).*
Sheng et al., Genomic and evolutionary characterization of a novel influenza-C-like virus from swine. Archives of Virology Feb. 2014, vol. 159, Issue 2, pp. 249-255.*
Hause BM, et al., Characterization of a Novel Influenza Virus in Cattle and Swine: Proposal for a New Genus in the OrthomyxoviridaeFamily. 2014 mBio vol. 5 (2), no pages specified.*
Vanhee, M et al., Vet. Res. 40 (6) 63 (2009).*
Hessen, M. "In the clinic. Influenza." Annals of in•T Ernal Medicine, vol. 151, No. 9, Nov. 1, 2009.
Yuanji (Kuo Yuanchi) et al: "Isolation of Influenza C Virus from Pigs and Experimental Infection of Pigs with Influenza C Virus", Journal of General Virology, vol. 64, No. 1, Jan. 1, 1983, pp. 177-182.
Yuanji and Desselberger 1984, J. Gen. Virol. 65:1857-72.
Kimura et al. 1997, Virus Res. 48:71-9.
Yamaoka et al. 1991, J Gen Virol. 72:711-714.
Brown et al. 1995, Epidemiol. Infect. 114:511-20.
Ohwada et al. 1987, Microbiol Immunol 31:1173-80.
Ma et al. 2009, The Role of Swine in the Generation of Novel Influenza Viruses. This article is a US Government work and is in the public domain in the USA • Zoonoses Public Health.

* cited by examiner

*Primary Examiner* — Shanon A Foley
*Assistant Examiner* — Myron Hill
(74) *Attorney, Agent, or Firm* — Judy Jarecki-Black; Chad Kitchen; Merial, Inc.

(57) ABSTRACT

A novel influenza C virus with only low homology to any influenza C virus previously characterized. Challenge studies show that the virus can infect pigs and be transmitted between pigs. Additionally, influenza C is commonly thought of as a human pathogen and serological studies have been performed, looking at the incidence of antibodies against this virus in both pigs and humans. Approximately 10% of pigs and 30% of humans have antibodies to this virus. Additional experimental data show that the virus can infect and transmit in ferrets (a surrogate for human infection studies). In a third aspect, the present invention is the partial genome of this novel influenza C virus. In another aspect, the present invention is a method of detection in animals of this novel influenza C virus.

14 Claims, 4 Drawing Sheets

SEQUENCE LISTING

```
<160> NUMBER OF SEQ ID NOS: 27

<210> SEQ ID NO 1
<211> LENGTH: 20
<212> TYPE: DNA
<213> ORGANISM: artificial sequence
<220> FEATURE:
<223> OTHER INFORMATION: Influenza C virus primer

<400> SEQUENCE: 1

gctgtttgca agttgatggg                                                  20


<210> SEQ ID NO 2
<211> LENGTH: 21
<212> TYPE: DNA
<213> ORGANISM: Artificial Sequence
<220> FEATURE:
<223> OTHER INFORMATION: Influenza C virus primer

<400> SEQUENCE: 2

tgaaagcagg taactccaag g                                                21


<210> SEQ ID NO 3
<211> LENGTH: 23
<212> TYPE: DNA
<213> ORGANISM: Artificial Sequence
<220> FEATURE:
<223> OTHER INFORMATION: Influenza C virus primer

<400> SEQUENCE: 3

ttcaggcaag cacccgtagg att                                              23


<210> SEQ ID NO 4
<211> LENGTH: 2169
<212> TYPE: DNA
<213> ORGANISM: Influenza C virus

<400> SEQUENCE: 4

atgagatggg caatgggaag caagttccca attatggcaa acagagaaat tttggaagaa      60

gctgggatac cagaacaatg ggaagggata gacctttggt caaaaaagga tgatgtttca     120

aagttgggga tggtgttagc gtctccagca gccataactt actggaattt ttgtggacct     180

ggagtggaca attcttctgt aataaaagat gtttataaag caaaatttat gaaaaaagaa     240

agatggagag agactctatg gggaccaatg aactttgaat tggtgggtaa acaaagaaga     300

gtggttgaaa ctcaaccagt ggaaataaag ctaaaccaaa aagaaataaa agaactaacg     360

atgtgggttc tttttgaaga tgaagcaaac cttgcaagca aattcataca ggaaaatttc     420

tcacttgtcc tgtcattaag agaactttac aagggaaagg cagtaaataa agatgttgca     480

gctttcatga ttgcccacca attttctccc gagaagaggt tcttacccac ttttggcccc     540

attagaccag aaagaatgga gctactccac tgtttagggg gtgatttctg gaagatagag     600

gcagtaactg cagggagcct gaacgaagaa caaaagaaga gagatgttag agcagttgct     660

agaaaaattt gccttagagc aagtgtggac ttatttactc cagcagagaa gataagggac     720

tatatagcaa gtgtgacaat gagatttgga acagtagaaa gaacattcga agacgtaata     780

agaaacagtg atgacatatc tgcggaagta accttatgca aggcggcact tgggtgcgaa     840

ttgggcaaaa gcatgagctt tgggaatcta aatctgagga aagtcagtgg agaagcagaa     900
```

-continued

```
acaatggaaa aaacagtata ttggggatta aagcccataa aatataaatg ctggagagga     960

gaggaaacat tttattgtga actgaggaag gtaacttgta tgtttagaag gtctgaaggc    1020

ctagattggg ctaacattgg acctggttca cctgaagaaa gaagagagct tttggcaatg    1080

gtgatgatat tctgcagaga tgggagattc tttgaatctg caccagttaa tattgatgaa    1140

tcattcttta ggacaagact gaataaagaa ataccttatc aatatgtgct gctaaaatgg    1200

gtaaggcaat cgagagacaa cttggatgcc ttgttgagta caagaggact aatacctgct    1260

catattggac aattcggaaa aggaatggga atagatggaa gtagctcatc ttctatggtt    1320

tacaagggag tcatgttgtc gaagacaccg atagacatag tggagagcaa agagaagcac    1380

agactgtttt taaatgacaa tatagaagca gtgacagaga gaggagcaat ggttgcatcc    1440

ataatggacc tatcagagga taatagagaa acatttaacg atgtgacttt taaccatgtc    1500

gacttagctg ttctcaaaga tgaaaagact gcaataataa agatatatcg atcactagtg    1560

gaaagaataa acactgatga tgatggccta cctgctttga taatgggtaa aagatattta    1620

gagttgtatc aattagatga agtaaaagac gcggtcgggc taataccaaa aaggatgctg    1680

ggggcgtatt cctaccaagc aagacagctc atacagtcac agatcaaaaa tgacagttat    1740

agccttcctg aaataataaa gttactgccc ttctgttaca gccctccaaa gaaaatgtta    1800

tttgatggga ctttccattt caaaaatcaa atgtatgtta ggcctggaat aaacacaaac    1860

cttttcagtt ttagtaagac cgacaaaagc aagatatatg tgaacggaag cgcagtaaaa    1920

ataaagcttg tgctcggaga cgatgaaatg gacaccagtc ttgcctttgt tgaaggattt    1980

caagtttgtg aatatgatcc aagagcacct ttgataccaa gaagagattt gagactgatt    2040

gggttcggaa agaaagttag agtttttgtt ggtcagggac aggagaaaac cctggtgagg    2100

acgagctcca aaagagccgc ctcccatgat gtaagcaaaa acattcgtag aatgcgtctg    2160

gaagtttga                                                            2169
```

```
<210> SEQ ID NO 5
<211> LENGTH: 722
<212> TYPE: PRT
<213> ORGANISM: Influenza C virus

<400> SEQUENCE: 5

Met Arg Trp Ala Met Gly Ser Lys Phe Pro Ile Met Ala Asn Arg Glu
1               5                   10                  15

Ile Leu Glu Glu Ala Gly Ile Pro Glu Gln Trp Glu Gly Ile Asp Leu
            20                  25                  30

Trp Ser Lys Lys Asp Asp Val Ser Lys Leu Gly Met Val Leu Ala Ser
        35                  40                  45

Pro Ala Ala Ile Thr Tyr Trp Asn Phe Cys Gly Pro Gly Val Asp Asn
    50                  55                  60

Ser Ser Val Ile Lys Asp Val Tyr Lys Ala Lys Phe Met Lys Lys Glu
65                  70                  75                  80

Arg Trp Arg Glu Thr Leu Trp Gly Pro Met Asn Phe Glu Leu Val Gly
                85                  90                  95

Lys Gln Arg Arg Val Val Glu Thr Gln Pro Val Glu Ile Lys Leu Asn
            100                 105                 110

Gln Lys Glu Ile Lys Glu Leu Thr Met Trp Val Leu Phe Glu Asp Glu
        115                 120                 125

Ala Asn Leu Ala Ser Lys Phe Ile Gln Glu Asn Phe Ser Leu Val Leu
    130                 135                 140
```

-continued

```
Ser Leu Arg Glu Leu Tyr Lys Gly Lys Ala Val Asn Lys Asp Val Ala
145                 150                 155                 160

Ala Phe Met Ile Ala His Gln Phe Ser Pro Glu Lys Arg Phe Leu Pro
                165                 170                 175

Thr Phe Gly Pro Ile Arg Pro Glu Arg Met Glu Leu Leu His Cys Leu
            180                 185                 190

Gly Gly Asp Phe Trp Lys Ile Glu Ala Val Thr Ala Gly Ser Leu Asn
        195                 200                 205

Glu Glu Gln Lys Lys Arg Asp Val Arg Ala Val Ala Arg Lys Ile Cys
    210                 215                 220

Leu Arg Ala Ser Val Asp Leu Phe Thr Pro Ala Glu Lys Ile Arg Asp
225                 230                 235                 240

Tyr Ile Ala Ser Val Thr Met Arg Phe Gly Thr Val Glu Arg Thr Phe
                245                 250                 255

Glu Asp Val Ile Arg Asn Ser Asp Asp Ile Ser Ala Glu Val Thr Leu
            260                 265                 270

Cys Lys Ala Ala Leu Gly Cys Glu Leu Gly Lys Ser Met Ser Phe Gly
        275                 280                 285

Asn Leu Asn Leu Arg Lys Val Ser Gly Glu Ala Glu Thr Met Glu Lys
    290                 295                 300

Thr Val Tyr Trp Gly Leu Lys Pro Ile Lys Tyr Lys Cys Trp Arg Gly
305                 310                 315                 320

Glu Glu Thr Phe Tyr Cys Glu Leu Arg Lys Val Thr Cys Met Phe Arg
                325                 330                 335

Arg Ser Glu Gly Leu Asp Trp Ala Asn Ile Gly Pro Gly Ser Pro Glu
            340                 345                 350

Glu Arg Arg Glu Leu Leu Ala Met Val Met Ile Phe Cys Arg Asp Gly
        355                 360                 365

Arg Phe Phe Glu Ser Ala Pro Val Asn Ile Asp Glu Ser Phe Phe Arg
    370                 375                 380

Thr Arg Leu Asn Lys Glu Ile Pro Tyr Gln Tyr Val Leu Leu Lys Trp
385                 390                 395                 400

Val Arg Gln Ser Arg Asp Asn Leu Asp Ala Leu Leu Ser Thr Arg Gly
                405                 410                 415

Leu Ile Pro Ala His Ile Gly Gln Phe Gly Lys Gly Met Gly Ile Asp
            420                 425                 430

Gly Ser Ser Ser Ser Ser Met Val Tyr Lys Gly Val Met Leu Ser Lys
        435                 440                 445

Thr Pro Ile Asp Ile Val Glu Ser Lys Glu Lys His Arg Leu Phe Leu
    450                 455                 460

Asn Asp Asn Ile Glu Ala Val Thr Glu Arg Gly Ala Met Val Ala Ser
465                 470                 475                 480

Ile Met Asp Leu Ser Glu Asp Asn Arg Glu Thr Phe Asn Asp Val Thr
                485                 490                 495

Phe Asn His Val Asp Leu Ala Val Leu Lys Asp Glu Lys Thr Ala Ile
            500                 505                 510

Ile Lys Ile Tyr Arg Ser Leu Val Glu Arg Ile Asn Thr Asp Asp Asp
        515                 520                 525

Gly Leu Pro Ala Leu Ile Met Gly Lys Arg Tyr Leu Glu Leu Tyr Gln
    530                 535                 540

Leu Asp Glu Val Lys Asp Ala Val Gly Leu Ile Pro Lys Arg Met Leu
545                 550                 555                 560
```

-continued

```
Gly Ala Tyr Ser Tyr Gln Ala Arg Gln Leu Ile Gln Ser Gln Ile Lys
                565                 570                 575

Asn Asp Ser Tyr Ser Leu Pro Glu Ile Ile Lys Leu Leu Pro Phe Cys
            580                 585                 590

Tyr Ser Pro Pro Lys Lys Met Leu Phe Asp Gly Thr Phe His Phe Lys
        595                 600                 605

Asn Gln Met Tyr Val Arg Pro Gly Ile Asn Thr Asn Leu Phe Ser Phe
    610                 615                 620

Ser Lys Thr Asp Lys Ser Lys Ile Tyr Val Asn Gly Ser Ala Val Lys
625                 630                 635                 640

Ile Lys Leu Val Leu Gly Asp Asp Glu Met Asp Thr Ser Leu Ala Phe
                645                 650                 655

Val Glu Gly Phe Gln Val Cys Glu Tyr Asp Pro Arg Ala Pro Leu Ile
            660                 665                 670

Pro Arg Arg Asp Leu Arg Leu Ile Gly Phe Gly Lys Lys Val Arg Val
        675                 680                 685

Phe Val Gly Gln Gly Gln Glu Lys Thr Leu Val Arg Thr Ser Ser Lys
    690                 695                 700

Arg Ala Ala Ser His Asp Val Ser Lys Asn Ile Arg Arg Met Arg Leu
705                 710                 715                 720

Glu Val
```

<210> SEQ ID NO 6
<211> LENGTH: 2163
<212> TYPE: DNA
<213> ORGANISM: Influenza C virus

<400> SEQUENCE: 6

```
atgtcacatg gaacatcgac caaatactca atggagactg tgtcaagaac ttactcctac     60

agtagaacta aaaaagaggt accttcggga atattcccaa tagagagaag gaaattctgt    120

aacacaatag aagacaaaga aaacctagaa aaaccgaatg gaaatgttga tataaatttc    180

atgttatcgc tggcagaaat gctggaagaa aagatgggga aagggttctt caaattctgt    240

gccaatgaag ctgaagctga aattttgaag atgcacttca gcaagctcac tgaaggaagg    300

caaacttatg actggacaag tgaaagaaat atgccagcag ccaccgctct tcagctaaca    360

gtagacgcta tacaagaaac acagggaaca ttcaaaggaa ctaccatggt tgaatattgc    420

aacaagatat tagaaatgat ggattggccg gaagtgaaat tcaaaaaggt cagaatgatt    480

gttcagaggc attgggaccc gaaaaccaaa aaagaaataa aaatgaagtc tccaacattg    540

atgataacaa agattggaag agaagaattc ataaagagga tatgcacgat aaataccatg    600

gccaaagacg gagaaagagg aaaatacaaa agaagagcta tagccacccc cgggatggga    660

atcaggccat tctcaaaaat tgtggaaact ttagcacaaa agatttgtga gagactagca    720

gagagcggtt tgcctgttgg gggaaatgag aagaaagcca aactaaaaac tacggtctct    780

tcaacaaact caaaactaca agaagggcag ttcatggtaa acataacagg ggacaacagc    840

aagtggaatg aatgtcagca accagaagct tatcttgcaa tgttggcata cattactaaa    900

gacagcagca acttaatgaa agatctctgc tcagtagcac caacattgtt ctgcaataag    960

tacgtaaaaa tgggacaagg tttccgagca aaaaacaaaa gaaaaaccaa agaaatagtg   1020

atacccgcaa aaaagatgaa agaaaggaaa gaattgatga acgcggaatg gagggaccta   1080

tttgaaacaa tagaacctta catggatgga gagtgctgct tcttgggggg aggaatgctg   1140

atgggaatgt ttaacatgtt gtcaactgtt tttggagtca tgacattcat gacattaagc   1200
```

-continued

```
attacagagg aactgkawgs aytggccaga aggaactgtt actggactgg gctacaaagt   1260

tcagatgatt ttgtgctctt ttgcatctct aggacttggc cagagatgga gatgactatt   1320

ctaaaattca tcgctgtttg caagttgatg ggaataaaca tgtctttgga aaaatcctac   1380

gggtgcttgc ctgaactttt tgagttcaca agcatgttct tttccgggga ttttgtctca   1440

aacatagcct tggagttacc tgctttcaca acagctggaa tgaatgaagg aaccgacttc   1500

acagctgcga tgtctgtcat aagaacaaac atgattaata atggactttc tcctgggact   1560

gctttaatgg ccctgcgaat ttgtctgcag gaatttagag caacatacag agtacaccct   1620

tatgattctg gagtgaagaa tcatcgaatg aaaatcataa ggaaattcat tgaaactatt   1680

gaaaacaaag atggattgct gatatcagat ggcgggaaat taatgaacaa tatctcaagt   1740

ttgcacatcc ctgaagaaat attgaaagag gatttgatgg atccctccta caggaacaga   1800

gttttcaatc ctaggaaccc ctttacacag tttgagaaga cagttgacat ctttaaggca   1860

agtggaccta taagggtaga ggagaacgag gcagttgtat caacgcattc ctttagaaca   1920

aggagcaata ggacattgct aaatacagac atgagggcaa tggctctcga agagaaaaga   1980

taccaagttg tttgcaacat gtaccgatcg gtcttcgaaa gtgcagacgt taacacccca   2040

ataggatcaa tgtcgatggg agaggcaatt gaagccaaaa tccttgaccg ggccagaacc   2100

cagtttgaaa atggaatcat agggggagaa gaatwttctg wwatyaaacr acgcaaagct   2160

taa                                                                 2163
```

<210> SEQ ID NO 7
<211> LENGTH: 720
<212> TYPE: PRT
<213> ORGANISM: Influenza C virus
<220> FEATURE:
<221> NAME/KEY: misc_feature
<222> LOCATION: (406)..(408)
<223> OTHER INFORMATION: Xaa can be any naturally occurring amino acid
<220> FEATURE:
<221> NAME/KEY: misc_feature
<222> LOCATION: (712)..(712)
<223> OTHER INFORMATION: Xaa can be any naturally occurring amino acid
<220> FEATURE:
<221> NAME/KEY: misc_feature
<222> LOCATION: (714)..(715)
<223> OTHER INFORMATION: Xaa can be any naturally occurring amino acid
<220> FEATURE:
<221> NAME/KEY: misc_feature
<222> LOCATION: (717)..(717)
<223> OTHER INFORMATION: Xaa can be any naturally occurring amino acid

<400> SEQUENCE: 7

```
Met Ser His Gly Thr Ser Thr Lys Tyr Ser Met Glu Thr Val Ser Arg
1               5                   10                  15

Thr Tyr Ser Tyr Ser Arg Thr Lys Lys Glu Val Pro Ser Gly Ile Phe
            20                  25                  30

Pro Ile Glu Arg Arg Lys Phe Cys Asn Thr Ile Glu Asp Lys Glu Asn
        35                  40                  45

Leu Glu Lys Pro Asn Gly Asn Val Asp Ile Asn Phe Met Leu Ser Leu
    50                  55                  60

Ala Glu Met Leu Glu Glu Lys Met Gly Lys Gly Phe Phe Lys Phe Cys
65                  70                  75                  80

Ala Asn Glu Ala Glu Ala Glu Ile Leu Lys Met His Phe Ser Lys Leu
                85                  90                  95

Thr Glu Gly Arg Gln Thr Tyr Asp Trp Thr Ser Glu Arg Asn Met Pro
            100                 105                 110
```

-continued

```
Ala Ala Thr Ala Leu Gln Leu Thr Val Asp Ala Ile Gln Glu Thr Gln
        115                 120                 125

Gly Thr Phe Lys Gly Thr Thr Met Val Glu Tyr Cys Asn Lys Ile Leu
    130                 135                 140

Glu Met Met Asp Trp Pro Glu Val Lys Phe Lys Lys Val Arg Met Ile
145                 150                 155                 160

Val Gln Arg His Trp Asp Pro Lys Thr Lys Lys Glu Ile Lys Met Lys
                165                 170                 175

Ser Pro Thr Leu Met Ile Thr Lys Ile Gly Arg Glu Glu Phe Ile Lys
            180                 185                 190

Arg Ile Cys Thr Ile Asn Thr Met Ala Lys Asp Gly Glu Arg Gly Lys
        195                 200                 205

Tyr Lys Arg Arg Ala Ile Ala Thr Pro Gly Met Gly Ile Arg Pro Phe
    210                 215                 220

Ser Lys Ile Val Glu Thr Leu Ala Gln Lys Ile Cys Glu Arg Leu Ala
225                 230                 235                 240

Glu Ser Gly Leu Pro Val Gly Gly Asn Glu Lys Lys Ala Lys Leu Lys
                245                 250                 255

Thr Thr Val Ser Ser Thr Asn Ser Lys Leu Gln Glu Gly Gln Phe Met
            260                 265                 270

Val Asn Ile Thr Gly Asp Asn Ser Lys Trp Asn Glu Cys Gln Gln Pro
        275                 280                 285

Glu Ala Tyr Leu Ala Met Leu Ala Tyr Ile Thr Lys Asp Ser Ser Asn
    290                 295                 300

Leu Met Lys Asp Leu Cys Ser Val Ala Pro Thr Leu Phe Cys Asn Lys
305                 310                 315                 320

Tyr Val Lys Met Gly Gln Gly Phe Arg Ala Lys Asn Lys Arg Lys Thr
                325                 330                 335

Lys Glu Ile Val Ile Pro Ala Lys Lys Met Lys Glu Arg Lys Glu Leu
            340                 345                 350

Met Asn Ala Glu Trp Arg Asp Leu Phe Glu Thr Ile Glu Pro Tyr Met
        355                 360                 365

Asp Gly Glu Cys Cys Phe Leu Gly Gly Gly Met Leu Met Gly Met Phe
    370                 375                 380

Asn Met Leu Ser Thr Val Phe Gly Val Met Thr Phe Met Thr Leu Ser
385                 390                 395                 400

Ile Thr Glu Glu Leu Xaa Xaa Xaa Ala Arg Arg Asn Cys Tyr Trp Thr
                405                 410                 415

Gly Leu Gln Ser Ser Asp Asp Phe Val Leu Phe Cys Ile Ser Arg Thr
            420                 425                 430

Trp Pro Glu Met Glu Met Thr Ile Leu Lys Phe Ile Ala Val Cys Lys
        435                 440                 445

Leu Met Gly Ile Asn Met Ser Leu Glu Lys Ser Tyr Gly Cys Leu Pro
    450                 455                 460

Glu Leu Phe Glu Phe Thr Ser Met Phe Phe Ser Gly Asp Phe Val Ser
465                 470                 475                 480

Asn Ile Ala Leu Glu Leu Pro Ala Phe Thr Thr Ala Gly Met Asn Glu
                485                 490                 495

Gly Thr Asp Phe Thr Ala Ala Met Ser Val Ile Arg Thr Asn Met Ile
            500                 505                 510

Asn Asn Gly Leu Ser Pro Gly Thr Ala Leu Met Ala Leu Arg Ile Cys
        515                 520                 525
```

-continued

```
Leu Gln Glu Phe Arg Ala Thr Tyr Arg Val His Pro Tyr Asp Ser Gly
    530                 535                 540

Val Lys Asn His Arg Met Lys Ile Ile Arg Lys Phe Ile Glu Thr Ile
545                 550                 555                 560

Glu Asn Lys Asp Gly Leu Leu Ile Ser Asp Gly Gly Lys Leu Met Asn
                565                 570                 575

Asn Ile Ser Ser Leu His Ile Pro Glu Glu Ile Leu Lys Glu Asp Leu
            580                 585                 590

Met Asp Pro Ser Tyr Arg Asn Arg Val Phe Asn Pro Arg Asn Pro Phe
        595                 600                 605

Thr Gln Phe Glu Lys Thr Val Asp Ile Phe Lys Ala Ser Gly Pro Ile
    610                 615                 620

Arg Val Glu Glu Asn Glu Ala Val Val Ser Thr His Ser Phe Arg Thr
625                 630                 635                 640

Arg Ser Asn Arg Thr Leu Leu Asn Thr Asp Met Arg Ala Met Ala Leu
                645                 650                 655

Glu Glu Lys Arg Tyr Gln Val Val Cys Asn Met Tyr Arg Ser Val Phe
            660                 665                 670

Glu Ser Ala Asp Val Asn Thr Pro Ile Gly Ser Met Ser Met Gly Glu
        675                 680                 685

Ala Ile Glu Ala Lys Ile Leu Asp Arg Ala Arg Thr Gln Phe Glu Asn
    690                 695                 700

Gly Ile Ile Gly Gly Glu Glu Xaa Ser Xaa Xaa Lys Xaa Arg Lys Ala
705                 710                 715                 720
```

<210> SEQ ID NO 8
<211> LENGTH: 2133
<212> TYPE: DNA
<213> ORGANISM: Influenza C virus

<400> SEQUENCE: 8

```
atgtctagtg taatcagaga aatcgcaaag cgattcttgg aacaagcaac gataaacatc     60

gctgaagaag tggtcagaga atatggagac catgaaagaa caatgatatc tgttggagtt    120

catttccaag cttgctgcct tataagtgat gaatataccc ttgaggatga gacaacccca    180

agatacgttc ttttggaggg attgaaaaga caagaggcta taagcaagca gaataacatt    240

tgctccactt tgggattgga gcccttgaga aatctagcag atatttttga tcgaaaaaca    300

agaagattcc ttgaggtagg aattacaaag agagaatccg atgagtatta ccaggaaaag    360

ttcaacaaaa taggaaatga catggacata catgttttca catatgaagg caaatatttc    420

agcaacaatc ccaatgggtt ggaagacatc caaaagacaa gaatttttac attcctatct    480

tttgtgtcag acgaattgag aaaagagaac atgttcacag aaatgtatgt tacagaagaa    540

ggggcacctg aacttgaaat gtacaagtca aagcttttca ttgcgatgag agacgagagc    600

gtgcctttgc cttacataaa ctatgagcac cttaggacaa gatgtgaaac attcaaaaga    660

aatcaggctg aatgcgaagc aaaggtagcg gatgtggctt cacggctaaa aatcaaactg    720

gaacatctag aagaaaataa actgcggccg ctagagatac cgaaggagaa agaggctccc    780

tatacacaca aatttttgat gaaagatgct tggttctttg caaaacctca tgattcggag    840

agagcacaac cgcaacagat attgtatgat ttctttgaag cagcaaacat ggggttcatg    900

acgacatccc caaaaccgat attcggaaag caaggactga tgtatcactc cctctggggg    960

cagacaaaaa gagcaataaa ggacaagaga aatgagttgg agccttcaga acagagagac   1020

ttcctttgtg gaattggaag agcctccaag aaaatacagg aggacaaatg gcaagaatcc   1080
```

-continued

```
agagaggaag agtttaaaca agaagagact aaaggggcag ctaagagggg gttcccaaca   1140

tggtttaatg aagaatggct ttgggcaatg agggactcag gggatgggga caataaaata   1200

ggggattgga tacccatggc agaaatgcct ccctgcaaga atgagatgga agattatgca   1260

aaaaagatgt gtgaagaatt agaatccaaa atacagggaa caaattgtgc tagggaaatg   1320

tccaagttga tacatacaat tgggagctta catacagaat gtaggaactt tcccggaaag   1380

gtcaagatag tgcctatata ctgcagaggg acactgagag gggaatcaac tgactgtttg   1440

tttggaatag caataaaagg gaaatcccat ttaaacaaag atgatggaat gtatactgtt   1500

gtaacttttg agttttccac tgaagaacca aatccaagca aacatgaaaa atatacggtc   1560

ttcgaagctg gaacagtgcc tgtggaagcc gtggtgttaa ctcccaaaag ggaaagagtt   1620

ctcaaagaga agaaattgtt cctttattgc agaactactg gaatgagcaa gttaaagaac   1680

gattggtttt ctaaatgcag gagatgtctt ataccaacaa tggagactgt agagcagata   1740

gtgctgaaag aatgcgctct gaaagaagaa aacagagttt cagagatgtt ggagaataag   1800

agagcttgga ttgcccatga gaacggagag aatcttacaa gattggtatc aacaaagctc   1860

aaggacttgt gtagaatgct aattgtgaca caattttatt actgtatata taacgacaat   1920

caattggaag gattctgtaa cgagcaaaag aaattcctta tgtttcttca agcagataag   1980

gactcaaaat ctgcatttac ttttaatcag aaagggttat atgaaaaaat tgaagagtgt   2040

attgtcagca atccattatg tattttccta gctgataggc taaacaaatt atttcttgta   2100

gccaagtcca atggagctaa gtactttgaa tga                                2133
```

<210> SEQ ID NO 9
<211> LENGTH: 710
<212> TYPE: PRT
<213> ORGANISM: Influenza C virus

<400> SEQUENCE: 9

```
Met Ser Ser Val Ile Arg Glu Ile Ala Lys Arg Phe Leu Glu Gln Ala
1               5                   10                  15

Thr Ile Asn Ile Ala Glu Glu Val Val Arg Glu Tyr Gly Asp His Glu
            20                  25                  30

Arg Thr Met Ile Ser Val Gly Val His Phe Gln Ala Cys Cys Leu Ile
        35                  40                  45

Ser Asp Glu Tyr Thr Leu Glu Asp Glu Thr Thr Pro Arg Tyr Val Leu
    50                  55                  60

Leu Glu Gly Leu Lys Arg Gln Glu Ala Ile Ser Lys Gln Asn Asn Ile
65                  70                  75                  80

Cys Ser Thr Leu Gly Leu Glu Pro Leu Arg Asn Leu Ala Asp Ile Phe
                85                  90                  95

Asp Arg Lys Thr Arg Arg Phe Leu Glu Val Gly Ile Thr Lys Arg Glu
            100                 105                 110

Ser Asp Glu Tyr Tyr Gln Glu Lys Phe Asn Lys Ile Gly Asn Asp Met
        115                 120                 125

Asp Ile His Val Phe Thr Tyr Glu Gly Lys Tyr Phe Ser Asn Asn Pro
    130                 135                 140

Asn Gly Leu Glu Asp Ile Gln Lys Thr Arg Ile Phe Thr Phe Leu Ser
145                 150                 155                 160

Phe Val Ser Asp Glu Leu Arg Lys Glu Asn Met Phe Thr Glu Met Tyr
                165                 170                 175

Val Thr Glu Glu Gly Ala Pro Glu Leu Glu Met Tyr Lys Ser Lys Leu
            180                 185                 190
```

-continued

```
Phe Ile Ala Met Arg Asp Glu Ser Val Pro Leu Pro Tyr Ile Asn Tyr
        195                 200                 205

Glu His Leu Arg Thr Arg Cys Glu Thr Phe Lys Arg Asn Gln Ala Glu
    210                 215                 220

Cys Glu Ala Lys Val Ala Asp Val Ala Ser Arg Leu Lys Ile Lys Leu
225                 230                 235                 240

Glu His Leu Glu Glu Asn Lys Leu Arg Pro Leu Glu Ile Pro Lys Glu
                245                 250                 255

Lys Glu Ala Pro Tyr Thr His Lys Phe Leu Met Lys Asp Ala Trp Phe
            260                 265                 270

Phe Ala Lys Pro His Asp Ser Glu Arg Ala Gln Pro Gln Gln Ile Leu
        275                 280                 285

Tyr Asp Phe Phe Glu Ala Ala Asn Met Gly Phe Met Thr Thr Ser Pro
    290                 295                 300

Lys Pro Ile Phe Gly Lys Gln Gly Leu Met Tyr His Ser Leu Trp Gly
305                 310                 315                 320

Gln Thr Lys Arg Ala Ile Lys Asp Lys Arg Asn Glu Leu Glu Pro Ser
                325                 330                 335

Glu Gln Arg Asp Phe Leu Cys Gly Ile Gly Arg Ala Ser Lys Lys Ile
            340                 345                 350

Gln Glu Asp Lys Trp Gln Glu Ser Arg Glu Glu Glu Phe Lys Gln Glu
        355                 360                 365

Glu Thr Lys Gly Ala Ala Lys Arg Gly Phe Pro Thr Trp Phe Asn Glu
    370                 375                 380

Glu Trp Leu Trp Ala Met Arg Asp Ser Gly Asp Gly Asp Asn Lys Ile
385                 390                 395                 400

Gly Asp Trp Ile Pro Met Ala Glu Met Pro Pro Cys Lys Asn Glu Met
                405                 410                 415

Glu Asp Tyr Ala Lys Lys Met Cys Glu Glu Leu Glu Ser Lys Ile Gln
            420                 425                 430

Gly Thr Asn Cys Ala Arg Glu Met Ser Lys Leu Ile His Thr Ile Gly
        435                 440                 445

Ser Leu His Thr Glu Cys Arg Asn Phe Pro Gly Lys Val Lys Ile Val
    450                 455                 460

Pro Ile Tyr Cys Arg Gly Thr Leu Arg Gly Glu Ser Thr Asp Cys Leu
465                 470                 475                 480

Phe Gly Ile Ala Ile Lys Gly Lys Ser His Leu Asn Lys Asp Asp Gly
                485                 490                 495

Met Tyr Thr Val Val Thr Phe Glu Phe Ser Thr Glu Glu Pro Asn Pro
            500                 505                 510

Ser Lys His Glu Lys Tyr Thr Val Phe Glu Ala Gly Thr Val Pro Val
        515                 520                 525

Glu Ala Val Val Leu Thr Pro Lys Arg Glu Arg Val Leu Lys Glu Lys
    530                 535                 540

Lys Leu Phe Leu Tyr Cys Arg Thr Thr Gly Met Ser Lys Leu Lys Asn
545                 550                 555                 560

Asp Trp Phe Ser Lys Cys Arg Arg Cys Leu Ile Pro Thr Met Glu Thr
                565                 570                 575

Val Glu Gln Ile Val Leu Lys Glu Cys Ala Leu Lys Glu Glu Asn Arg
            580                 585                 590

Val Ser Glu Met Leu Glu Asn Lys Arg Ala Trp Ile Ala His Glu Asn
        595                 600                 605
```

-continued

```
Gly Glu Asn Leu Thr Arg Leu Val Ser Thr Lys Leu Lys Asp Leu Cys
    610                 615                 620

Arg Met Leu Ile Val Thr Gln Phe Tyr Tyr Cys Ile Tyr Asn Asp Asn
625                 630                 635                 640

Gln Leu Glu Gly Phe Cys Asn Glu Gln Lys Lys Phe Leu Met Phe Leu
                645                 650                 655

Gln Ala Asp Lys Asp Ser Lys Ser Ala Phe Thr Phe Asn Gln Lys Gly
            660                 665                 670

Leu Tyr Glu Lys Ile Glu Glu Cys Ile Val Ser Asn Pro Leu Cys Ile
        675                 680                 685

Phe Leu Ala Asp Arg Leu Asn Lys Leu Phe Leu Val Ala Lys Ser Asn
    690                 695                 700

Gly Ala Lys Tyr Phe Glu
705                 710


<210> SEQ ID NO 10
<211> LENGTH: 1911
<212> TYPE: DNA
<213> ORGANISM: Influenza C virus

<400> SEQUENCE: 10

atgtttttgc ttctagcaac aattacagca ataactgctt gccaagcaga aagagaactg      60

atatgcatag tgcaaagagt gaatgaaagc ttctctcttc actctggatt tggaggaaat     120

gtttacagca tgaagactga gccaatgact ggattcacaa acgtgaccaa aggtgctagt     180

gtcatcaacc aaaaagactg gattggattc ggagattcaa gaacagactt gactaatgat     240

cagtttccag cgtcttcaga tgttccattg gcagtggcga agaagtttcg gtcattgtca     300

ggggcttcgt tgatgttgtc agcttttggg cctcctggca aggttgacta cctctatcaa     360

ggatgtggga aagaaaaagt attttatgaa ggggtaaact ggtcccctga ggcaggaatt     420

gattgctttg gatcaaactg gactcagaca aagaaggact tctattcgag gatatatgaa     480

gctgctagaa gcagcacatg catgactctt gtaaattctc ttgacaccaa gatatcatca     540

acaacagcca cggctggaac cgcatcttct tgttcttcaa gttggatgaa aagcccgttg     600

tggtatgcag aatcttctgt taatcctgga gctaaacctc aagtttgtgg gactgagcaa     660

tcggcaactt ttactttgcc gacaagcttc ggaatttaca aatgcaacaa gcatgtagtg     720

cagctttgtt actttgtgta cgaaaacaaa gcaaaattta acacttttgg ctgtggagat     780

tattaccaaa attactatga tgggaatgga aacctgatag ggggaatgga taacagagtg     840

gcagcataca gaggaatagc aaacgctgga gttaaaattg aatgtccttc caaaatcttg     900

aaccctggga cttacagcat taaatcaaca ccaagattcc ttctagtacc aaaaaggtca     960

tactgcttcg acactgatgg agggtaccct atacaagtag ttcaatctga gtrgtcakct    1020

tsacgawgrt cagmtwcayg magatcagat aatgccacag aagaagcatg cctacaaaca    1080

gaaggatgta ttttcatcaa aaagacaacc ccttatgtag gagaagcaga tgacaaccat    1140

ggagacattg agatgaggca actcttgagt gggcttggca acaacgacac agtgtgcgtt    1200

tcccaaagtg gatacacaaa aggagagacc ccttttgtaa aggattattt gagtcctccc    1260

aagtatggca gatgtcagtt gaaaactgac agtggaagaa tcccaactct accttctggg    1320

ttgataatac cgcaagcagg gactgactct ttaatgagaa ctttgacgcc agcaacaagg    1380

atcttcggaa tagatgactt aatcttcggg cttttattcg tggggtttgt cgcaggaggg    1440

gtcgcaggag gttacttctg ggaagatcaa aatggagggg gtggtggtgc ctcggtgagc    1500
```

-continued

```
agtacgcagg ctggatttga caaaatcgga aaagatatac agcagcttcg gaatgacaca   1560

aatgcagcaa ttgaaggctt caacgggaga attgcccatg atgagcaags cattaagart   1620

ttggcaaaag aawtcgaara wgcaagsgma gakgcwwkgg yagaggcttt ggtaggggaa   1680

cttggtataa taagatccct catagttgcc aacataagca tgaatctaaa agaatcttta   1740

tatgaactag caaaccaaat aacaaaaaga ggaggaggaa ttgcacaaga agsaggccma   1800

kkgyrywrga wgcagrccca gggtgttggt atgttgactc cgaaaactgt gatgcaagct   1860

gcaaagagta cattttcaac ttcaatggaa gtgccactgt ccccacattg a            1911
```

<210> SEQ ID NO 11
<211> LENGTH: 636
<212> TYPE: PRT
<213> ORGANISM: Influenza C virus
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (340)..(341)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (345)..(347)
<223> OTHER INFORMATION: Xaa can be any naturally occurring amino acid
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (549)..(551)
<223> OTHER INFORMATION: Xaa can be any naturally occurring amino acid
<220> FEATURE:
<221> NAME/KEY: misc_feature
<222> LOCATION: (553)..(554)
<223> OTHER INFORMATION: Xaa can be any naturally occurring amino acid
<220> FEATURE:
<221> NAME/KEY: misc_feature
<222> LOCATION: (598)..(598)
<223> OTHER INFORMATION: Xaa can be any naturally occurring amino acid
<220> FEATURE:
<221> NAME/KEY: misc_feature
<222> LOCATION: (600)..(604)
<223> OTHER INFORMATION: Xaa can be any naturally occurring amino acid
<220> FEATURE:
<221> NAME/KEY: misc_feature
<222> LOCATION: (606)..(606)
<223> OTHER INFORMATION: Xaa can be any naturally occurring amino acid

<400> SEQUENCE: 11

```
Met Phe Leu Leu Leu Ala Thr Ile Thr Ala Ile Thr Ala Cys Gln Ala
1               5                   10                  15

Glu Arg Glu Leu Ile Cys Ile Val Gln Arg Val Asn Glu Ser Phe Ser
            20                  25                  30
```

-continued

```
Leu His Ser Gly Phe Gly Gly Asn Val Tyr Ser Met Lys Thr Glu Pro
        35                  40                  45

Met Thr Gly Phe Thr Asn Val Thr Lys Gly Ala Ser Val Ile Asn Gln
    50                  55                  60

Lys Asp Trp Ile Gly Phe Gly Asp Ser Arg Thr Asp Leu Thr Asn Asp
65                  70                  75                  80

Gln Phe Pro Ala Ser Ser Asp Val Pro Leu Ala Val Ala Lys Lys Phe
                85                  90                  95

Arg Ser Leu Ser Gly Ala Ser Leu Met Leu Ser Ala Phe Gly Pro Pro
            100                 105                 110

Gly Lys Val Asp Tyr Leu Tyr Gln Gly Cys Gly Lys Glu Lys Val Phe
        115                 120                 125

Tyr Glu Gly Val Asn Trp Ser Pro Glu Ala Gly Ile Asp Cys Phe Gly
    130                 135                 140

Ser Asn Trp Thr Gln Thr Lys Lys Asp Phe Tyr Ser Arg Ile Tyr Glu
145                 150                 155                 160

Ala Ala Arg Ser Ser Thr Cys Met Thr Leu Val Asn Ser Leu Asp Thr
                165                 170                 175

Lys Ile Ser Ser Thr Thr Ala Thr Ala Gly Thr Ala Ser Ser Cys Ser
            180                 185                 190

Ser Ser Trp Met Lys Ser Pro Leu Trp Tyr Ala Glu Ser Ser Val Asn
        195                 200                 205

Pro Gly Ala Lys Pro Gln Val Cys Gly Thr Glu Gln Ser Ala Thr Phe
    210                 215                 220

Thr Leu Pro Thr Ser Phe Gly Ile Tyr Lys Cys Asn Lys His Val Val
225                 230                 235                 240

Gln Leu Cys Tyr Phe Val Tyr Glu Asn Lys Ala Lys Phe Asn Thr Phe
                245                 250                 255

Gly Cys Gly Asp Tyr Tyr Gln Asn Tyr Tyr Asp Gly Asn Gly Asn Leu
            260                 265                 270

Ile Gly Gly Met Asp Asn Arg Val Ala Ala Tyr Arg Gly Ile Ala Asn
        275                 280                 285

Ala Gly Val Lys Ile Glu Cys Pro Ser Lys Ile Leu Asn Pro Gly Thr
    290                 295                 300

Tyr Ser Ile Lys Ser Thr Pro Arg Phe Leu Leu Val Pro Lys Arg Ser
305                 310                 315                 320

Tyr Cys Phe Asp Thr Asp Gly Gly Tyr Pro Ile Gln Val Val Gln Ser
                325                 330                 335

Glu Xaa Ser Xaa Xaa Arg Xaa Ser Xaa Xaa Xaa Arg Ser Asp Asn Ala
            340                 345                 350

Thr Glu Glu Ala Cys Leu Gln Thr Glu Gly Cys Ile Phe Ile Lys Lys
        355                 360                 365

Thr Thr Pro Tyr Val Gly Glu Ala Asp Asp Asn His Gly Asp Ile Glu
    370                 375                 380

Met Arg Gln Leu Leu Ser Gly Leu Gly Asn Asn Asp Thr Val Cys Val
385                 390                 395                 400

Ser Gln Ser Gly Tyr Thr Lys Gly Glu Thr Pro Phe Val Lys Asp Tyr
                405                 410                 415

Leu Ser Pro Pro Lys Tyr Gly Arg Cys Gln Leu Lys Thr Asp Ser Gly
            420                 425                 430

Arg Ile Pro Thr Leu Pro Ser Gly Leu Ile Ile Pro Gln Ala Gly Thr
        435                 440                 445
```

-continued

```
Asp Ser Leu Met Arg Thr Leu Thr Pro Ala Thr Arg Ile Phe Gly Ile
    450                 455                 460

Asp Asp Leu Ile Phe Gly Leu Leu Phe Val Gly Phe Val Ala Gly Gly
465                 470                 475                 480

Val Ala Gly Gly Tyr Phe Trp Gly Arg Ser Asn Gly Gly Gly Gly Gly
                485                 490                 495

Ala Ser Val Ser Ser Thr Gln Ala Gly Phe Asp Lys Ile Gly Lys Asp
            500                 505                 510

Ile Gln Gln Leu Arg Asn Asp Thr Asn Ala Ala Ile Glu Gly Phe Asn
        515                 520                 525

Gly Arg Ile Ala His Asp Glu Gln Xaa Ile Lys Xaa Leu Ala Lys Glu
    530                 535                 540

Xaa Glu Xaa Ala Xaa Xaa Xaa Ala Xaa Xaa Glu Ala Leu Val Gly Glu
545                 550                 555                 560

Leu Gly Ile Ile Arg Ser Leu Ile Val Ala Asn Ile Ser Met Asn Leu
                565                 570                 575

Lys Glu Ser Leu Tyr Glu Leu Ala Asn Gln Ile Thr Lys Arg Gly Gly
            580                 585                 590

Gly Ile Ala Gln Glu Xaa Gly Xaa Xaa Xaa Xaa Xaa Gln Xaa Gln Gly
        595                 600                 605

Val Gly Met Leu Thr Pro Lys Thr Val Met Gln Ala Ala Lys Ser Thr
    610                 615                 620

Phe Ser Thr Ser Met Glu Val Pro Leu Ser Pro His
625                 630                 635


<210> SEQ ID NO 12
<211> LENGTH: 1659
<212> TYPE: DNA
<213> ORGANISM: Influenza C virus

<400> SEQUENCE: 12

atggactcaa caaaagccca aacgcctgaa gagcagagag caaagaatgc caaaaccatc      60

cttgagaaca tacagatata tgaaaggatg tgtgatctct ttggggtgtc agaagatgac     120

aaactgataa ttgagaacag tatttcaatt gagaggatga taagagttgt aacagataag     180

aaataccaag acaaaaaact aaagaatgct ggaagtgatc ctgaaaagat tgcaaatgca     240

gggaaagttt tctgtcgatt ggtggagtca acagctggga aatgtagtgc aagattggga     300

atggcactga aacccaacgt tgaggcagtc ctgaccgatg tactcgggaa tgaactggat     360

agggctgctg tgcttgggaa aagaatgggg ttttcagcaa tgttcaaatc aaacctggaa     420

gaggttttgt accaaagagg aaagaatcag cttaaaaaga ggaatgctgc agaaactttc     480

actctttcac aaggtgcttc gctagaggca agatttaggc ccataatgga aaaacaccta     540

ggtgttggga ctgttgtggc gtcaataaag aatatcctgg caagcaaaaa gaacgggaac     600

tacaggaaca agatggtgag gaaacctgga ggaaacagag agagctggtc accattggag     660

agagagatat cctttctgaa caagaagttg tttcctggac caatgaggca gctctgcaag     720

aaattcgaat acttgaacga gcaagagaag caactggcct taaaccttat gctggatgca     780

agtctcatcc taaaaccgca agtgactcac aaaatgataa tgccttggtc aatgtggctg     840

gctgtgaaga agtatgcaga aatgaacaag ggatcaccca gtcttgaaga cctcgcagcc     900

tattctggag taagagcctt tatggccttc aatacagctt gctacatgag taaattcacc     960

attgggaagg gaattgtggg agatgcagag atcatggaaa atggaaacga caagatgcaa    1020

actcttgcaa tggcttgttt tggactggcg tatgaagaca ccgggattgt tgctgcaatg    1080
```

-continued

```
atctcccaac ccatgaagaa aagatatcag ttgagagtgg ggaacttcaa tcctccagaa   1140

aaaggaacaa taaaaggaac aagcgccggc tatttccaca agtgggctga atttggaaat   1200

aggctgcctt tcaacagttt tggaactggt gaatccaaac agataagcaa ctcaggagtg   1260

tttgcagtgc agaggcccag cactactaac attcaaagac tggcagagct aatggctagg   1320

aataccggag aaaccagcga caactttact cagttggttc agaaaataag agaacaagtg   1380

ggggcctttg ctgatcaaaa agcaaatctt cgagagttca ccggaggata tatttatgac   1440

attactgacg taacgaagag caacccccaag atacctcagt tgggtgggga ctctttcttc   1500

tttgagttca ccggaagcga cgttccaaga actggagcca aaagaagagt gggaggagct   1560

gatgatgtga cccctggaac ttcccagccc aagaaaagag gaaggcaagg tgccggagca   1620

gwakcaagta tggacattga aacagttggt gaagattaa                          1659
```

<210> SEQ ID NO 13
<211> LENGTH: 552
<212> TYPE: PRT
<213> ORGANISM: Influenza C virus
<220> FEATURE:
<221> NAME/KEY: misc_feature
<222> LOCATION: (541)..(542)
<223> OTHER INFORMATION: Xaa can be any naturally occurring amino acid

<400> SEQUENCE: 13

```
Met Asp Ser Thr Lys Ala Gln Thr Pro Glu Glu Gln Arg Ala Lys Asn
1               5                   10                  15

Ala Lys Thr Ile Leu Glu Asn Ile Gln Ile Tyr Glu Arg Met Cys Asp
            20                  25                  30

Leu Phe Gly Val Ser Glu Asp Asp Lys Leu Ile Ile Glu Asn Ser Ile
        35                  40                  45

Ser Ile Glu Arg Met Ile Arg Val Val Thr Asp Lys Lys Tyr Gln Asp
    50                  55                  60

Lys Lys Leu Lys Asn Ala Gly Ser Asp Pro Glu Lys Ile Ala Asn Ala
65                  70                  75                  80

Gly Lys Val Phe Cys Arg Leu Val Glu Ser Thr Ala Gly Lys Cys Ser
                85                  90                  95

Ala Arg Leu Gly Met Ala Leu Lys Pro Asn Val Glu Ala Val Leu Thr
            100                 105                 110

Asp Val Leu Gly Asn Glu Leu Asp Arg Ala Ala Val Leu Gly Lys Arg
        115                 120                 125

Met Gly Phe Ser Ala Met Phe Lys Ser Asn Leu Glu Glu Val Leu Tyr
    130                 135                 140

Gln Arg Gly Lys Asn Gln Leu Lys Lys Arg Asn Ala Ala Glu Thr Phe
145                 150                 155                 160

Thr Leu Ser Gln Gly Ala Ser Leu Glu Ala Arg Phe Arg Pro Ile Met
                165                 170                 175

Glu Lys His Leu Gly Val Gly Thr Val Val Ala Ser Ile Lys Asn Ile
            180                 185                 190

Leu Ala Ser Lys Lys Asn Gly Asn Tyr Arg Asn Lys Met Val Arg Lys
        195                 200                 205

Pro Gly Gly Asn Arg Glu Ser Trp Ser Pro Leu Glu Arg Glu Ile Ser
    210                 215                 220

Phe Leu Asn Lys Lys Leu Phe Pro Gly Pro Met Arg Gln Leu Cys Lys
225                 230                 235                 240

Lys Phe Glu Tyr Leu Asn Glu Gln Glu Lys Gln Leu Ala Leu Asn Leu
                245                 250                 255
```

-continued

```
Met Leu Asp Ala Ser Leu Ile Leu Lys Pro Gln Val Thr His Lys Met
            260                 265                 270

Ile Met Pro Trp Ser Met Trp Leu Ala Val Lys Lys Tyr Ala Glu Met
        275                 280                 285

Asn Lys Gly Ser Pro Ser Leu Glu Asp Leu Ala Ala Tyr Ser Gly Val
    290                 295                 300

Arg Ala Phe Met Ala Phe Asn Thr Ala Cys Tyr Met Ser Lys Phe Thr
305                 310                 315                 320

Ile Gly Lys Gly Ile Val Gly Asp Ala Glu Ile Met Glu Asn Gly Asn
                325                 330                 335

Asp Lys Met Gln Thr Leu Ala Met Ala Cys Phe Gly Leu Ala Tyr Glu
            340                 345                 350

Asp Thr Gly Ile Val Ala Ala Met Ile Ser Gln Pro Met Lys Lys Arg
        355                 360                 365

Tyr Gln Leu Arg Val Gly Asn Phe Asn Pro Pro Glu Lys Gly Thr Ile
    370                 375                 380

Lys Gly Thr Ser Ala Gly Tyr Phe His Lys Trp Ala Glu Phe Gly Asn
385                 390                 395                 400

Arg Leu Pro Phe Asn Ser Phe Gly Thr Gly Glu Ser Lys Gln Ile Ser
                405                 410                 415

Asn Ser Gly Val Phe Ala Val Gln Arg Pro Ser Thr Thr Asn Ile Gln
            420                 425                 430

Arg Leu Ala Glu Leu Met Ala Arg Asn Thr Gly Glu Thr Ser Asp Asn
        435                 440                 445

Phe Thr Gln Leu Val Gln Lys Ile Arg Glu Gln Val Gly Ala Phe Ala
    450                 455                 460

Asp Gln Lys Ala Asn Leu Arg Glu Phe Thr Gly Gly Tyr Ile Tyr Asp
465                 470                 475                 480

Ile Thr Asp Val Thr Lys Ser Asn Pro Lys Ile Pro Gln Leu Gly Gly
                485                 490                 495

Asp Ser Phe Phe Phe Glu Phe Thr Gly Ser Asp Val Pro Arg Thr Gly
            500                 505                 510

Ala Lys Arg Arg Val Gly Gly Ala Asp Asp Val Thr Pro Gly Thr Ser
        515                 520                 525

Gln Pro Lys Lys Arg Gly Arg Gln Gly Ala Gly Ala Xaa Xaa Ser Met
    530                 535                 540

Asp Ile Glu Thr Val Gly Glu Asp
545                 550
```

<210> SEQ ID NO 14
<211> LENGTH: 1194
<212> TYPE: DNA
<213> ORGANISM: Influenza C virus

<400> SEQUENCE: 14

```
atggcacaag aacaactact tgctgaactt gagggatacc tcagaggagt taacccaatg      60

accaggcaaa cgattatgaa gtctgcaaga ggtgggatgg atagtgctaa ggaggcagca     120

aaagcagcga agaagggaga aatgcaacta acaagtggag agagcatagt ggtgcacata     180

tgcctgagag ccatgtaccc tggaataaag ccatggtcag aagccaaaaa agatcttgat     240

aaagctacag aaggactgag tggaaaagac tgcaaaaata taagaaaagc tctgaggaag     300

gcaggagacc tgacagggat aaaggagatg atgatgatgt atgaaatgag ggaggacaaa     360

aaagcagaaa tggtagagca aatctacgat gacccagagg attttacaga agatgtaagg     420
```

-continued

```
cttgggaccg ttgctgcctg gcttcaatgc aaaaacaaaa ggagcgagaa atatcatcac    480

aagatgtcaa tgtctggaag cactgcactt gccttgggag atgcccaaaa ggccggaatg    540

gccatagaaa atatggctag tgttgtgcca atgaaaaaag aggcccaggc actgcacaaa    600

gacgcagaag ttttgattga actggcaaga atagcatatg ggtcaagagc aatggaaggg    660

cacctgcaaa atgcaatgga cggaattgga agcaaagtca gtggaatggc taatcttgcc    720

ctaaaaaggt cagttcttac tttgttaatg ttggtaattt gtgggatccc cacttgtgta    780

aatgctgaaa ctgtggaaga attttgtaga aagaaactaa atcagacgga agaaaaggtt    840

tatgtccatt gtttcaatga ggatgatggt cgggcaatga ctttagctgc tttgatactt    900

ggatgcttta gtatgcttta cattttaata aaggcaatac tgatgctttt gttgacaatc    960

ataaatggaa gaccaaatgg aagttgggat gacttgaaac atgttgtaaa atgtttttca   1020

gagactggaa gtgagaactt cgccagggat ataatggtcc tggaatccag gcgagatggg   1080

gaggagacaa gctccccaga ggagggacta ggccctccat tgagtggatt caatgaaatg   1140

gtgtattcat ggaaacatta tatccctggc gaagttctcw cttccagtct ctga         1194
```

```
<210> SEQ ID NO 15
<211> LENGTH: 397
<212> TYPE: PRT
<213> ORGANISM: Influenza C virus
<220> FEATURE:
<221> NAME/KEY: misc_feature
<222> LOCATION: (394)..(394)
<223> OTHER INFORMATION: Xaa can be any naturally occurring amino acid

<400> SEQUENCE: 15

Met Ala Gln Glu Gln Leu Leu Ala Glu Leu Glu Gly Tyr Leu Arg Gly
1               5                   10                  15

Val Asn Pro Met Thr Arg Gln Thr Ile Met Lys Ser Ala Arg Gly Gly
            20                  25                  30

Met Asp Ser Ala Lys Glu Ala Ala Lys Ala Ala Lys Lys Gly Glu Met
        35                  40                  45

Gln Leu Thr Ser Gly Glu Ser Ile Val Val His Ile Cys Leu Arg Ala
    50                  55                  60

Met Tyr Pro Gly Ile Lys Pro Trp Ser Glu Ala Lys Lys Asp Leu Asp
65                  70                  75                  80

Lys Ala Thr Glu Gly Leu Ser Gly Lys Asp Cys Lys Asn Ile Arg Lys
                85                  90                  95

Ala Leu Arg Lys Ala Gly Asp Leu Thr Gly Ile Lys Glu Met Met Met
            100                 105                 110

Met Tyr Glu Met Arg Glu Asp Lys Lys Ala Glu Met Val Glu Gln Ile
        115                 120                 125

Tyr Asp Asp Pro Glu Asp Phe Thr Glu Asp Val Arg Leu Gly Thr Val
    130                 135                 140

Ala Ala Trp Leu Gln Cys Lys Asn Lys Arg Ser Glu Lys Tyr His His
145                 150                 155                 160

Lys Met Ser Met Ser Gly Ser Thr Ala Leu Ala Leu Gly Asp Ala Gln
                165                 170                 175

Lys Ala Gly Met Ala Ile Glu Asn Met Ala Ser Val Val Pro Met Lys
            180                 185                 190

Lys Glu Ala Gln Ala Leu His Lys Asp Ala Glu Val Leu Ile Glu Leu
        195                 200                 205

Ala Arg Ile Ala Tyr Gly Ser Arg Ala Met Glu Gly His Leu Gln Asn
    210                 215                 220
```

-continued

```
Ala Met Asp Gly Ile Gly Ser Lys Val Ser Gly Met Ala Asn Leu Ala
225                 230                 235                 240

Leu Lys Arg Ser Val Leu Thr Leu Leu Met Leu Val Ile Cys Gly Ile
                245                 250                 255

Pro Thr Cys Val Asn Ala Glu Thr Val Glu Glu Phe Cys Arg Lys Lys
            260                 265                 270

Leu Asn Gln Thr Glu Glu Lys Val Tyr Val His Cys Phe Asn Glu Asp
        275                 280                 285

Asp Gly Arg Ala Met Thr Leu Ala Ala Leu Ile Leu Gly Cys Phe Ser
    290                 295                 300

Met Leu Tyr Ile Leu Ile Lys Ala Ile Leu Met Leu Leu Leu Thr Ile
305                 310                 315                 320

Ile Asn Gly Arg Pro Asn Gly Ser Trp Asp Asp Leu Lys His Val Val
                325                 330                 335

Lys Cys Phe Ser Glu Thr Gly Ser Glu Asn Phe Ala Arg Asp Ile Met
            340                 345                 350

Val Leu Glu Ser Arg Arg Asp Gly Glu Glu Thr Ser Ser Pro Glu Glu
        355                 360                 365

Gly Leu Gly Pro Pro Leu Ser Gly Phe Asn Glu Met Val Tyr Ser Trp
    370                 375                 380

Lys His Tyr Ile Pro Gly Glu Val Leu Xaa Ser Ser Leu
385                 390                 395
```

<210> SEQ ID NO 16
<211> LENGTH: 732
<212> TYPE: DNA
<213> ORGANISM: Influenza C virus

<400> SEQUENCE: 16

```
atgtctgaaa ataagtcagt gaacacaaca aatatcagag cagcaatctc cgaattggca     60

ttgggcgcag ccagctggat ggattcctct gggttaatga ctttcgagaa aatgagaaag    120

tctgctgaga attcactgag agtcgaacag gtttatgaac cgagaacttg ggaagatgca    180

gtggctgaag gtagagaaat tctaggattc actactattg ctgccttaag aaaaccagag    240

gagactcatg ctgttgaatt ggggaagaac attatctatc ccttaggagg aaaccctttc    300

tatctaagcc catgtaccat tgacactctg tatgagccaa agctcataag acaaggagaa    360

gtctttggag taaaatatcg gaactgcaat tgctttgtaa aaactgctga actattagtg    420

accgacatgg gagaaatcat tgtgctcttt tgcagaaaca ctgagaaacc agcttactgc    480

cttaagaatt tccgtagagg agatgaccca gagaagtcag tacgaaagat actcagaatt    540

tggagaagtg gacttgttgt tgccgttgat gcggaatcta gagatgaaat cagacgatac    600

aaatctggat gtgaaacaga tcccttctgg agaagagaag gcgcaactac tggagaggtt    660

caggagttgc ttggtgtcat tgataaggtt gaaatccaag ctgggagtag cgatggtgaa    720

ctctttgact aa                                                         732
```

<210> SEQ ID NO 17
<211> LENGTH: 243
<212> TYPE: PRT
<213> ORGANISM: Influenza C virus -continued

<400> SEQUENCE: 17

Met Ser Glu Asn Lys Ser Val Asn Thr Thr Asn Ile Arg Ala Ala Ile
1 5 10 15

Ser Glu Leu Ala Leu Gly Ala Ala Ser Trp Met Asp Ser Ser Gly Leu
20 25 30

Met Thr Phe Glu Lys Met Arg Lys Ser Ala Glu Asn Ser Leu Arg Val
35 40 45

Glu Gln Val Tyr Glu Pro Arg Thr Trp Glu Asp Ala Val Ala Glu Gly
50 55 60

Arg Glu Ile Leu Gly Phe Thr Thr Ile Ala Ala Leu Arg Lys Pro Glu
65 70 75 80

Glu Thr His Ala Val Glu Leu Gly Lys Asn Ile Ile Tyr Pro Leu Gly
85 90 95

Gly Asn Pro Phe Tyr Leu Ser Pro Cys Thr Ile Asp Thr Leu Tyr Glu
100 105 110

Pro Lys Leu Ile Arg Gln Gly Glu Val Phe Gly Val Lys Tyr Arg Asn
115 120 125

Cys Asn Cys Phe Val Lys Thr Ala Glu Leu Leu Val Thr Asp Met Gly
130 135 140

Glu Ile Ile Val Leu Phe Cys Arg Asn Thr Glu Lys Pro Ala Tyr Cys
145 150 155 160

Leu Lys Asn Phe Arg Arg Gly Asp Asp Pro Glu Lys Ser Val Arg Lys
165 170 175

Ile Leu Arg Ile Trp Arg Ser Gly Leu Val Val Ala Val Asp Ala Glu
180 185 190

Ser Arg Asp Glu Ile Arg Arg Tyr Lys Ser Gly Cys Glu Thr Asp Pro
195 200 205

Phe Trp Arg Arg Glu Gly Ala Thr Thr Gly Glu Val Gln Glu Leu Leu
210 215 220

Gly Val Ile Asp Lys Val Glu Ile Gln Ala Gly Ser Ser Asp Gly Glu
225 230 235 240

Leu Phe Asp

<210> SEQ ID NO 18
<211> LENGTH: 168
<212> TYPE: PRT
<213> ORGANISM: Influenza C virus

<400> SEQUENCE: 18

Met Ser Glu Asn Lys Ser Val Asn Thr Thr Asn Ile Arg Ala Ala Ile
1 5 10 15

Ser Glu Leu Ala Leu Gly Ala Ala Ser Trp Met Asp Ser Ser Gly Leu
20 25 30

Met Thr Phe Glu Lys Met Arg Lys Ser Ala Glu Asn Ser Leu Arg Val
35 40 45

Glu Gln Val Tyr Glu Pro Arg Thr Trp Glu Asp Ala Val Ala Glu Met
50 55 60

Thr Gln Arg Ser Gln Tyr Glu Arg Tyr Ser Glu Phe Gly Glu Val Asp
65 70 75 80

Leu Leu Leu Pro Leu Met Arg Asn Leu Glu Met Lys Ser Asp Asp Thr
85 90 95

Asn Leu Asp Val Lys Gln Ile Pro Ser Gly Glu Glu Lys Ala Gln Leu
100 105 110

-continued

```
Leu Glu Arg Phe Arg Ser Cys Leu Val Ser Leu Ile Arg Leu Lys Ser
        115                 120                 125

Lys Leu Gly Val Ala Met Val Asn Ser Leu Thr Asn Gln Asp Met Arg
    130                 135                 140

Ala Ala Leu Asp Glu Ile Lys Ser Val Ser Arg Thr Ile Ser Met Leu
145                 150                 155                 160

Lys Glu Cys Ile Arg Ser Leu Val
                165
```

<210> SEQ ID NO 19
<211> LENGTH: 24
<212> TYPE: DNA
<213> ORGANISM: Artificial Sequence
<220> FEATURE:
<223> OTHER INFORMATION: Swine influenza A virus forward primer

<400> SEQUENCE: 19
agatgagtct tctaaccgag gtcg 24

<210> SEQ ID NO 20
<211> LENGTH: 24
<212> TYPE: DNA
<213> ORGANISM: Artificial Sequence
<220> FEATURE:
<223> OTHER INFORMATION: Swine Influenza A virus reverse primer

<400> SEQUENCE: 20
tgcaaaaaca tcttcaagtc tctg 24

<210> SEQ ID NO 21
<211> LENGTH: 20
<212> TYPE: DNA
<213> ORGANISM: Artificial Sequence
<220> FEATURE:
<223> OTHER INFORMATION: Swine Influenza A virus probe (not including
the 5' Cy3 and 3' IABkQ)

<400> SEQUENCE: 21
tcaggccccc tcaaagccga 20

<210> SEQ ID NO 22
<211> LENGTH: 22
<212> TYPE: DNA
<213> ORGANISM: Artificial Sequence
<220> FEATURE:
<223> OTHER INFORMATION: Human influenza B virus forward primer

<400> SEQUENCE: 22
tcctcaactc actcttcgag cg 22

<210> SEQ ID NO 23
<211> LENGTH: 21
<212> TYPE: DNA
<213> ORGANISM: Artificial Sequence
<220> FEATURE:
<223> OTHER INFORMATION: Human influenza B virus reverse primer

<400> SEQUENCE: 23
cggtgctctt gaccaaattg g 21

<210> SEQ ID NO 24
<211> LENGTH: 27
<212> TYPE: DNA
<213> ORGANISM: Artificial Sequence -continued

```
<220> FEATURE:
<223> OTHER INFORMATION: Human influenza B virus probe (not including
      the 5'-FAM and 3'-IABkQ)

<400> SEQUENCE: 24

ccaattcgag cagctgaaac tgcggtg                                    27


<210> SEQ ID NO 25
<211> LENGTH: 20
<212> TYPE: DNA
<213> ORGANISM: Artificial Sequence
<220> FEATURE:
<223> OTHER INFORMATION: Human influenza C virus forward primer

<400> SEQUENCE: 25

attgagagca ggaacgactg                                            20


<210> SEQ ID NO 26
<211> LENGTH: 20
<212> TYPE: DNA
<213> ORGANISM: Artificial Sequence
<220> FEATURE:
<223> OTHER INFORMATION: Human influenza C virus reverse primer

<400> SEQUENCE: 26

tcttaaaggc ccaggaaacg                                            20


<210> SEQ ID NO 27
<211> LENGTH: 23
<212> TYPE: DNA
<213> ORGANISM: Artificial Sequence
<220> FEATURE:
<223> OTHER INFORMATION: Human influenza C virus (not including the
      5'-FAM and 3'-IABkQ)

<400> SEQUENCE: 27

cccctctgga aagagccatg caa                                        23
```

INFLUENZA C VIRUS AND VACCINE

BACKGROUND OF THE INVENTION

Influenza C is a common pathogen of humans as most individuals are infected as children. Influenza C causes a mild respiratory disease similar to the common cold. There is one report of influenza C being isolated from pigs in China (Yuanji and Desselberger 1984, J. Gen. Virol. 65:1857-72). Additionally, this work demonstrated that porcine influenza C viruses could infect and transmit between pigs. Several other papers have identified antibodies in pigs that react with influenza C, suggesting that either pigs are a reservoir for influenza C or that humans very commonly pass this virus to pigs (Kimura et al. 1997, Virus Res. 48:71-9; Yamaoka et al. 1991, J Gen Virol. 72:711-714; Brown et al. 1995, Epidemiol. Infect. 114:511-20; Ohwada et al. 1987, Microbiol Immunol. 31:1173-80).

SUMMARY OF THE INVENTION

As influenza C has only been reported in one paper, it is rare to find in pigs. The virus that has been isolated and characterized is a very unique variant of influenza C. The overall percent homology of this virus to known influenza C viruses is only about 65%, showing that this is a completely new lineage of virus that has never been described and is only distantly related to described viruses. This low level of homology suggests that vaccines made against typical human influenza C viruses would not protect against C/swine/Oklahoma/1334/2011. The finding that "universal" influenza C primer sets also failed to detect this virus also speaks to its novelty. Additionally, the finding of antibody titers in humans and pigs, as well as the virus' ability to replicate in both pigs and ferrets, suggests that this virus is capable of causing disease in pigs and man. We show that we can create a vaccine that protects pigs from infection and the scientific literature would also support that this vaccine would protect humans.

In one aspect, the present invention is a novel influenza C virus with only low homology to any influenza C virus previously characterized. Challenge studies show that the virus can infect pigs and be transmitted between pigs. Additionally, influenza C is commonly thought of as a human pathogen and serological studies have been performed, looking at the incidence of antibodies against this virus in both pigs and humans. Approximately 10% of pigs and 30% of humans have antibodies to this virus. Additional experimental data show that the virus can infect and transmit in ferrets (a surrogate for human infection studies).

In a second aspect, the present invention is a vaccine to this novel influenza C virus.

In a third aspect, the present invention is the partial genome of this novel influenza C virus.

In another aspect, the present invention is a method of detection in animals of this novel influenza C virus.

DETAILED DESCRIPTION OF A PREFERRED EMBODIMENT

Isolation of the Virus

Figure 1:
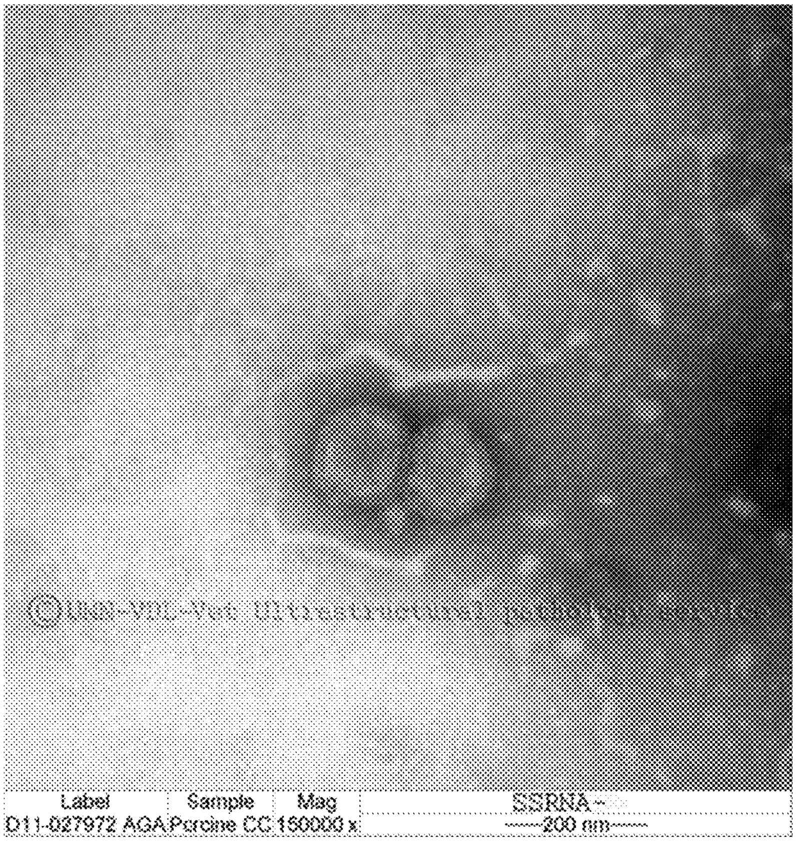
FIG. 1 is an electron microscopic photograph of the novel influenza C virus of the present invention.
Figure 2:
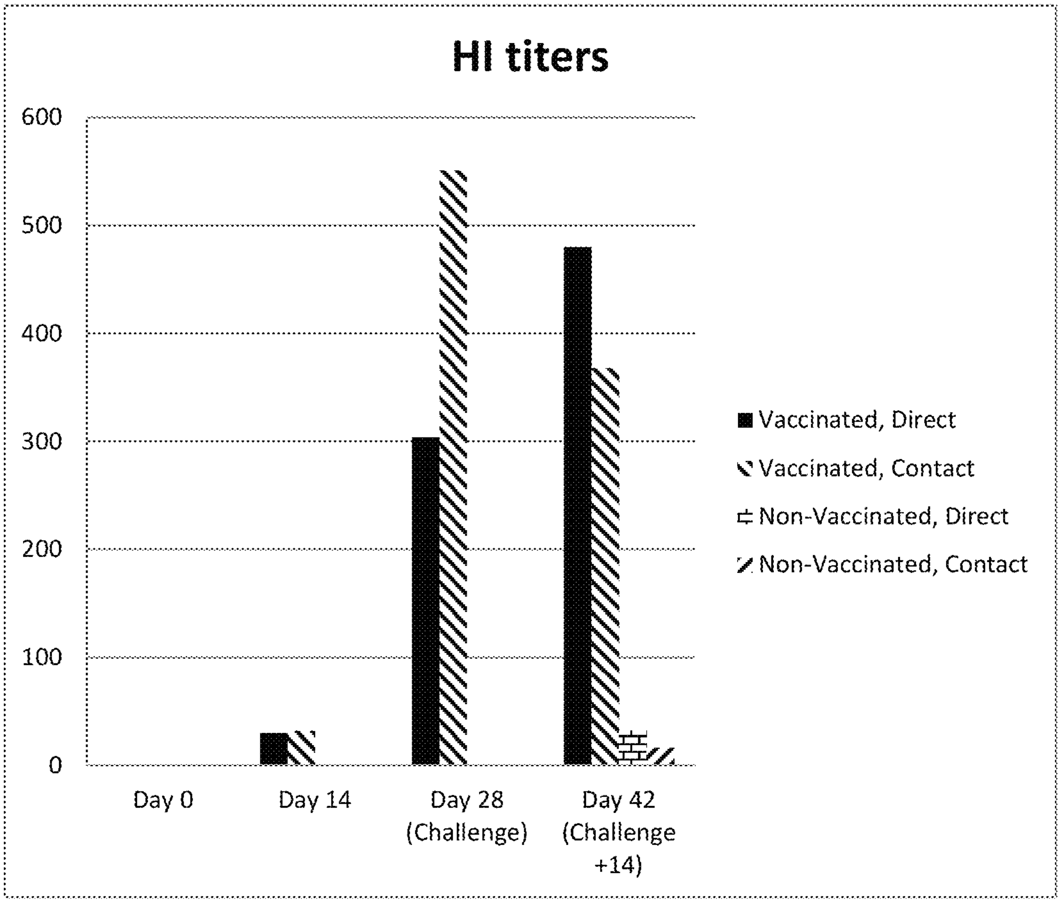
FIG. 2 is a graph showing the HI Titer in vaccinated and non-vaccinated pigs.

Samples submitted to Newport Laboratories were nasal swabs from pigs displaying signs of influenza-like illness. Samples were negative for influenza A by real time reverse transcription PCR. An aliquot of the sample was applied to a confluent monolayer of Swine Testicle (ST) cells to attempt to grow any viruses that were present. After 5 days cytopathic effects were evident, indicating that a virus was growing in the swine testicle cells. Samples of cell culture supernatant were analyzed for influenza A by QPCR and were negative. Cell culture supernatant was analyzed for the ability to hemagglutinate turkey red blood cells (hemagglutination assay). The hemagglutination assay was carried out according to the following protocol (Experiment #1).

EXPERIMENT #1

1.0 Introduction

To quantitate Swine Influenza Virus.

2.0 Materials

Reservoir 96-well microtiter V bottom plates

Multi-channel pipettor and tips (10-200 μL)

100-1000 μL pipettor 10-100 μL pipettor

Pipette Tips

Personal Protective Equipment (PPE: lab coat, safety glasses, gloves)

Biosafety Cabinet

Cover plate/lid

Timer 50 mL falcon tube

Centrifuge 3.0 Reagents/Media

Turkey Red Blood Cells (TRBC) from Lampire

1×DPBS 4.0 Media Formulations

Turkey Red Blood Cell Solution (0.5%)

TRBC arrive in Alsevers solution. Centrifuge in 50 mL conical tubes at 2000 rpm for 10 minutes. Aspirate and discard the supernatant.

Wash the RBC by adding 1×DPBS equal to volume of blood started with. Invert and shake gently. Centrifuge and discard the supernatant. Repeat two more times. Store packed cells at 4° C.

Add 50 mL 1×DPBS into 50 mL tube. Take out 250 μL 1×PBS. Add 250 μL of Turkey packed RBC. Mix gently. 5 mLs is needed per plate. Store diluted cells at 4° C.

5.0 Procedure

Preparation

Eight samples will run horizontally on a 96 well plate. Figure out how many plates are needed based on samples to be tested and fill out the appropriate paperwork.

Alternative set-up: Twelve samples can be run vertically on a 96 well plate.

Test Procedure

Fill all wells of plates with 50 μL DPBS.

Put 50 μL of sample #1 into well A1; sample #2 into B1, etc.

With each test set of plates, run a negative control on the last plate (just DBPS).

With 50 μL, dilute the plates starting from column 1 through 12 (excluding negative control row), discarding the remaining 50 μL.

After the plate is diluted, fill all wells with 50 μL of 0.5% TRBC (invert tube to mix blood cells, do not vortex). Tap plates gently, cover and incubate at room temperature up to 2 hours.

Alternative set-up: To run twelve samples vertically, put 50 μL of sample #1 into well A1; sample #2 into A2.

With 50 μL, dilute the plates starting from row A through row H (excluding negative control column), discarding the remaining 50 μL.

After the plate is diluted, fill all wells with 50 μL of 0.5% TRBC (invert tube to mix blood cells, do not vortex). Tap plates gently, cover and incubate at room temperature up to 2 hours.

6.0 Reading

Tilt the plates at 30-45° to read. When reading, the last well without a complete teardrop is the end point. Mark on the corresponding paperwork.

HA titers are listed on the corresponding paperwork

Negative control row (or column) should completely tear drop, showing no hemagglutination.

The unidentified virus had the ability to hemagglutinate crbc's with a titer of 1280. Many viruses contain a gene encoding a hemagglutinin protein which enables a virus to bind cells, including red blood cells. Influenza viruses have the ability to hemagglutinate red blood cells.

EXPERIMENT #2

A flask of ST cells infected with the unknown virus was sent to the University of Minnesota Veterinary Diagnostic Laboratory for electron microscopy. Images of the virus were consistent with the family Orthomyxoviridae (FIG. 1). This family consists of influenza A, B, C and thogoto virus.

EXPERIMENT #3

PCR was attempted with primers designed to specifically detect either influenza A, B or C (Table 1). All PCR reactions were negative. Additionally, a neuraminidase activity assay was performed using the neuraminidase substrate methylumbelliferyl N-acetylneuraminic acid. The virus did not possess neuraminidase activity (both influenza A and B have neuraminidases). An esterase activity assay was next performed with 4-nitrophenyl acetate (Sigma Aldrich N8130). The virus exhibited esterase activity. The ability to hemagglutinate red blood cells and having an esterase activity is characteristic of influenza C and some members of the family Coronaviridae. Based on the hemagglutinin esterase activity and electron microscopy, the virus was preliminarily identified as influenza C although the negative for influenza C by PCR.

EXPERIMENT #4—GENOME SEQUENCING

Virus was expanded in cell culture to generate 200 mL of cell culture harvest with a hemagglutination (HA) titer of 2560. Cell culture fluids were filtered through a 0.2 micron filter to remove cell debris. The fluids were then centrifuged at 110,000×g for 3 hours to pellet the virus. The virus was then resuspended in 1 mL of phosphate buffered saline and digested with DNase (New England Biolabs M0303S) and RNase (New England Biolabs M0243S) at 37 C for 1 hour. The viral solution was then gently layered on top of 35 mL of 25% sucrose solution and centrifuged for 3 hours at 110,000×g to pellet the virus. Viral RNA was extracted from the viral pellet using a Qiagen[trade] Viral RNA Mini Kit (Qiagen, Inc., 27220 Turnberry Lane Suite 200 Valencia, Calif. 91355) according to the manufacturer's instructions. In brief, the viral pellet was resuspended in 700 μL of buffer AVL containing carrier RNA and incubated for 10 minutes at room temperature. Next, 560 μL of ethanol was added to the sample and then sample was loaded onto a QIAamp™ mini column by centrifugation at 6000×g. The column was next washed sequentially with 500 μL each of buffers AW1 and AW2, dried by centrifugation at 14,000×g for 2 minutes and then eluted with 60 μL of water. cDNA was then reverse transcribed from the viral RNA using a Promega Reverse Transcription Kit (Promega Corp., 2800 Woods Hollow Rd., Madison Wis. 53711;) along with enclosed random primers. The GoScript™ Reverse Transcription System is a convenient kit that includes a reverse transcriptase and an optimized set of reagents designed for efficient synthesis of first-strand cDNA in preparation for PCR amplification. The components of the GoScript™ Reverse Transcription System can be used to reverse transcribe RNA templates starting with either total RNA, poly(A)+mRNA or synthetic transcript RNA.

The cDNA was next digested for 1 hour at 37C with RNaseH (New England Biolabs M0297S) to remove RNA from the RNA-cDNA hybrid. The single stranded cDNA was made double stranded using the Klenow fragment from DNA polymerase (New England Biolabs M0210S).

Using the BioRuptor® Sonication System (Diagenode Inc. North America, 376 Lafayette Rd., Suite 102, Sparta, N.J. 07871), the double stranded cDNA was sonicated to fragment the viral cDNA. The fragmented cDNA was next used to construct a cDNA library according to the Life Technologies™ Ion Plus Fragment Library Kit protocol and described

TABLE 1

Primers and probes used for real time reverse transcription PCR for virus detection. (IABkQ = Iowa black hole quencher)

| Virus | Forward Primer | Reverse Primer | Probe |
|---|---|---|---|
| Swine influenza A viruses | AGATGAGTCTTCTAACCG AGGTCG (SEQ ID NO: 19) | TGCAAAAACATCTTCAA GTCTCTG (SEQ ID NO: 20) | 5'-Cy3-TCA GGC CCC CTC AAA GCC GA-3'-IABkQ (SEQ ID NO: 21 with 5' Cy3 and 3' IABkQ) |
| Human influenza B viruses | TCCTCAACTCACTCTTCG AGCG (SEQ ID NO: 22) | CGGTGCTCTTGACCAAA TTGG (SEQ ID NO: 23) | 5'-FAM-CCA ATT CGA GCA GCT GAA ACT GCG GTG-3'-IABkQ (SEQ ID NO: 24 with 5' FAM and 3' IABkQ) |
| Human influenza C viruses | ATTGAGAGCAGGAACGA CTG(SEQ ID NO: 25) | TCTTAAAGGCCCAGGAA ACG(SEQ ID NO: 26) | 5'-FAM-CCCCTCTGGAAAGAGCC ATGCAA-3'-IABkQ (SEQ ID NO: 27 with 5' FAM and 3' IABkQ) |

by the following: 50 microliters of the fragmented cDNA was mixed with 108 microliters nuclease-free water, 40 microliters 5× End Repair Buffer, and 2 microliters of End Repair Enzyme. The reaction was incubated at room temperature for 20 minutes. Following incubation, 360 microliters of Agencourt® Ampure® beads were added to the sample, which was then placed on a rotator at 8-10 rpm for 10 minutes. The sample was pulse-spun and placed on a DynaMag™-2 magnet rack. After the solution cleared, the supernatant was removed and discarded. The sample was then twice washed using the subsequent protocol. 500 microliters of freshly made 70% ethanol were added to the sample without removing it from the magnet. The tube containing the sample was rotated twice on the magnet to move the beads around. After the solution cleared, the ethanol was removed. This wash procedure was repeated. Following the second 70% ethanol wash and removal of the supernatant, the sample tube was pulse-spun and placed back on the magnetic rack. Residual ethanol was aspirated and the sample dried at room temperature for approximately five minutes. 50 microliters of 1×TE (10 mM Tris-HCl, 1 mM EDTA, pH 8.0) were added to the cDNA and vortexed, pulse-spun, and placed back on the magnetic rack. After the solution cleared, the supernatant containing the eluted cDNA was transferred to a new 1.5-mL LoBind Tube[trade].

20 microliters of 10× Ligase Buffer, 77 microliters Nuclease-Free Water, 50 microliters of Adapters, and 3 microliters DNA Ligase were mixed with the 50 microliters of cDNA. The mixture was incubated at room temperature for 30 minutes. After the solution cleared, the supernatant was removed and discarded. The sample was then twice washed using the subsequent protocol: 500 microliters of freshly made 70% ethanol were added to the sample without removing it from the magnet. The tube containing the sample was rotated twice on the magnet to move the beads around. After the solution cleared, the ethanol was removed. This wash procedure was repeated. Following the second 70% ethanol wash and removal of the supernatant, the sample tube was pulse-spun and placed back on the magnetic rack. Residual ethanol was aspirated and the sample dried at room temperature for approximately five minutes. 30 microliters of 1×TE were added to the cDNA and vortexed, pulse-spun, and placed back on the magnetic rack. After the solution cleared, the supernatant containing the eluted cDNA was transferred to a new 1.5-mL LoBind Tube[trade].

All 30 microliters of cDNA were loaded onto a 2% agarose gel and subjected to gel electrophoresis for 80 minutes at 110V. Following gel electrophoresis, the sample was size-selected for 180-210 base pairs. The size-selected cDNA library was gel purified using the QIAquick[trade] PCR Purification Kit (Qiagen, Inc., 27220 Turnberry Lane Suite 200 Valencia, Calif. 91355) per the manufacturer's directions. The excised cDNA fragment of the gel was weighed and 3 volumes of Buffer QG to 1 volume gel were added. The mixture was incubated on a rotator at room temperature until the gel slice was completely dissolved. Once the gel slice had dissolved completely, the solution was applied to a QIAquick [trade] spin column (Qiagen, Inc., 27220 Turnberry Lane Suite 200 Valencia, Calif. 91355) and provided 2 milliliter collection tube and centrifuged at maximum speed (approximately 16,000 rcf) for 1 minute. The flow-through was discarded and the QIAquick[trade] column was placed back in the same tube. The column containing the cDNA was washed by adding 750 microliters Buffer PE to the column and centrifuging it at maximum speed for 1 minute. The flow-through was discarded and the QIAquick[trade] column was placed back in the same tube and centrifuged for 4 minutes at maximum speed. The QIAquick[trade] column was then put in a clean 1.5 milliliter microcentrifuge tube. 40 microliters of Buffer EB were added to the QIAquick[trade] column membrane and allowed to incubate at room temperature for several minutes before the column was centrifuged for 1 minute to elute the cDNA.

The eluted size-selected cDNA library was nick-translated and amplified according to the Life Technologies[trade] Ion Plus Fragment Library Kit protocol. 40 microliters of size-selected cDNA were mixed with 200 microliters Platinum [trade] PCR SuperMix High Fidelity and 10 microliters of Library Amplification Primer Mix. 125 microliter aliquots were transferred to each of 2 PCR tubes and ran on a thermocycler according to the following parameters:

TABLE 2

PCR Thermocycler Parameters

| Stage | Step | Temperature | Time |
|---|---|---|---|
| Holding | Nick Translation | 72° C. | 20 min |
| Holding | Denature | 95° C. | 5 min |
| Cycling (10 cycles) | Denature | 95° C. | 15 sec |
| | Anneal | 58° C. | 15 sec |
| | Extend | 72° C. | 1 min |
| Holding | — | 4° C. | ∞ |

The samples were pooled in a new 1.5 milliliter microcentrifuge tube and purified by adding 375 microliters of Agencourt Ampure® beads to the sample and incubating it for 10 minutes at room temperature on a rotator. The sample was pulse-spun and placed on a DynaMag[trade]-2 magnet rack. After the solution cleared, the supernatant was removed and discarded. The sample was then twice washed using the subsequent protocol. 500 microliters of freshly made 70% ethanol were added to the sample without removing it from the magnet. The tube containing the sample was rotated twice on the magnet to move the beads around. After the solution cleared, the ethanol was removed. This wash procedure was repeated. Following the second 70% ethanol wash and removal of the supernatant, the sample tube was pulse-spun and placed back on the magnetic rack. Residual ethanol was aspirated and the sample dried at room temperature for approximately five minutes. 50 microliters of 1×TE were added to the cDNA and vortexed, pulse-spun, and placed back on the magnetic rack. After the solution cleared, the supernatant containing the eluted cDNA was transferred to a new 1.5-mL LoBind Tube.

The amount of cDNA was quantified using the Ion Library Quantitation Kit according to the manufacturer's protocol. 5 sequential 10-fold dilutions were prepared from the *E. coli* DH10B Control Library according to the following table.

TABLE 3

Dilutions for *E. coli* DH10B Control Library

| Standard | Control Library | Nuclease-free Water | Fold Dilution |
|---|---|---|---|
| 1 | 5 microliters (undiluted) | 45 microliters | 0.1 |
| 2 | 5 microliters Std 1 | 45 microliters | 0.01 |
| 3 | 5 microliters Std 2 | 45 microliters | 0.001 |
| 4 | 5 microliters Std 3 | 45 microliters | 0.0001 |
| 5 | 5 microliters Std 4 | 45 microliters | 0.00001 |

A 1:20 dilution of the sample library in Nuclease-free water was initially prepared. Serial dilutions at 1:2000 and 1:20000 were subsequently prepared as described in the following table

TABLE 4

| Dilutions for Sample Library | | |
|---|---|---|
| Dilution | Library | Nuclease-Free Water |
| 1:2000 | 1 microliter of 1:20 | 99 microliters |
| 1:20000 | 5 microliters of 1:2000 | 45 microliters |

As each qPCR reaction was prepared in triplicate, the master mix was prepared by mixing 250 microliters of Ion Library TaqMan® qPCR Mix 2×, 25 microliters of Ion Library TaqMan® Quantitation Assay 20×, and 100 microliters of Nuclease-free water per qPCR reaction. For each reaction, 15 microliters of master mix was pipetted into a well of the PCR plate. 5 microliters of the diluted control or sample library were added to each appropriate well. 5 microliters of nuclease-free water was used as the no-template control (NTC). The wells were sealed, briefly centrifuged, and subjected to the following real-time PCR conditions.

TABLE 5

| PCR Conditions for qPCR Reaction | | |
|---|---|---|
| Stage | Temperature | Time |
| Hold | 50° C. | 2 minutes |
| Hold | 95° C. | 20 seconds |
| Cycle (40 cycles) | 95° C. | 3 seconds |
| | 60° C. | 30 seconds |

The Template Dilution Factor was calculated using the following equation:

Template Dilution Factor=[(*qPCR* relative quantity)*(sample library fold dilution)]/0.32

The sample was diluted accordingly and prepared for sequencing using the Ion Xpress™ Template Kit v2.0. The Emulsion Oil™ was removed from the fridge and mixed. 9 milliliters of Emulsion Oil™ were added to a IKA® DT-20 tube. The filled IKA® tube was placed on ice until ready for use. The aqueous PCR mix was generated by combining 582 microliters of Nuclease-free water, 200 microliters 5×PCR Reagent Mix, 100 microliters of 10×PCR Enzyme Mix, 100 microliters of Ion Sphere[trade] Particles (vortexed for 1 minute before addition), and 18 microliters of the diluted sample library. The mixture was vortexed for 5 seconds and set aside while the IKA® DT-20 tube containing the Emulsion Oil was positioned on the IKA® Ultra-Turrax® Tube Drive and locked in place. The adhesive label on the cap of the IKA® DT-20 tube was removed to expose the sample loading port. The START button on the IKA® Ultra-Turrax® was pushed and the entire volume of the aqueous PCR mix was dispensed through the opening in the blue cap of the IKA® DT-20 tube. After mixing for 5 minutes on the IKA® Ultra-Turrax® Tube Drive, the emulsion was placed on ice for approximately 5 minutes. A wide-bore tip was created by cutting approximately 5 mm from a pipette tip to transfer the emulsion. Using an Eppendorf® Repeater® Pipettor fitted with the wide-bore tip, the emulsion was drawn up and dispensed in 100 microliter increments to each well of a 96-well PCR plate until approximately 90 wells were filled. The 96-well plate was capped and loaded onto a thermal cycler according to the following PCR parameters

TABLE 6

| PCR Parameters for Sequencing | | | |
|---|---|---|---|
| Stage | Step | Temperature | Time |
| Hold | Denature | 94° C. | 6 minutes |
| Cycle (40 cycles) | Denature | 94° C. | 30 seconds |
| | Anneal | 58° C. | 30 seconds |
| | Extend | 72° C. | 90 seconds |
| Cycle (5 cycles) | Denature | 94° C. | 30 seconds |
| | Extend | 68° C. | 6 minutes |
| Hold | — | 10° C. | ∞ |

Following the PCR reaction, as much of the contents of the wells as possible were transferred using a multi-channel pipette to a multi-channel pipette reservoir. Approximately 1.2 milliliters of the emulsion were transferred to each of six 1.5-mL microcentrifuge tubes. All six microcentrifuge tubes were centrifuged for 2 minutes at 15,500×g to collect the emulsion. During centrifugation, the Breaking Solution™ was created by mixing 2 milliliters Recovery Solution™ and 6 milliliters of 1-butanol. The Breaking Solution™ was then vortexed for about 1 minute until a fine white emulsified material formed. After centrifugation of the emulsion, the clear top fraction of oil from each tube was removed. The 6 tubes containing the white emulsion were each treated with one milliliter of the Breaking Solution™, vortexed for 30 seconds, and centrifuged for 2 minutes at 15,500×g. After centrifugation, the top organic phase of each tube was removed. Each sample tube received 1 mL of Recovery Solution™, was vortexed for 30 seconds, and then centrifuged for 3 minutes at 15,500×g. The supernatant from each tube was removed until only approximately 100 microliters were left. Using the same pipette tip, the pellets in all six tubes were resuspended and transferred to a new 1.5 milliliter microcentrifuge tube. Three of the original tubes were rinsed with a single 200 microliter aliquot of Recovery Solution™. After the third tube was rinsed, the solution was transferred to the tube that contained the combined, resuspended pellets. This procedure was repeated on the three remaining tubes.

Recovery Solution™ was added to the combined tube until the total volume was 1.5 milliliters. The tube was then vortexed for 30 seconds and centrifuged at 15,500×g for 3 minutes. The supernatant was removed until only about 100 microliters were left. The remaining material was resuspended and transferred to a new 1.5 milliliter microcentrifuge tube. 100 microliters of Wash Solution™ was added to the original tube, rinsed, and then transferred to the new tube containing the sample. The sample was twice washed by adding 1 milliliter of Wash Solution™™, vortexing for 30 seconds, and then centrifuging the tube for 3 minutes at 15,500×g. The supernatant was removed until only 100 microliters remained. This wash procedure was repeated.

The template-positive Ion Sphere™ Particles enrichment was performed in accordance with the Ion Xpress™ Template Kit v2.0 protocol. The bottle containing the Dynabeads® MyOne™ Streptavidin C1 beads was vortexed. 10 microliters of MyOne™ beads were transferred to a 1.5 milliliter microcentrifuge tube, washed with 70 microliters of Wash Solution™, vortexed, and placed on a magnet for 2 minutes. The supernatant was then discarded. The MyOne™ beads were resuspended in 10 microliters of new Wash Solution™ and then transferred to the sample tube containing the Ion Sphere Particles™ (ISPs). To perform the capture, 100 microliters of Annealing Buffer™ were also added to the sample tube which was then placed on the rotator for 10 minutes at room temperature. The sample tube was centrifuged and placed on the magnet until the solution was clear. The supernatant was transferred to a tube labeled "Unbound." The beads were twice washed with 200 microliters of Wash Solution™, mixed, and placed back on the magnet before the supernatant was transferred to the "Unbound" tube. A fresh Melt-Off Solution™ was prepared by combining 200 microliters 1 M NaOH, 16 microliters of 10% Tween® 20 in molecular grade water, and 1.38 milliliters of molecular grade water. To elute the Ion Sphere Particles from the Dynabeads® MyOne[trade] Streptavidin C1 beads, 400 microliters of the Melt-Off Solution™ was added to the sample tube, mixed, and then placed on the rotator for 7 minutes. The supernatant was removed afterwards and placed into the tube labeled "Enriched-1." The "Enriched-1" tube was vortexed and then spun at 15,500×g for 4 minutes. All but 100 microliters of supernatant were then discarded. 1 milliliter of Wash Solution™ was then applied to the "Enriched-1" tube, vortexed, and spun at 15,500×g for 4 minutes. Once again, all but 100 microliters of supernatant was removed. The remaining sample was mixed and the "Enriched-1" tube was placed back on the magnet. The supernatant was removed after several minutes and put in a tube labeled "Enriched-2."

DNA sequencing was conducted in accordance with the Life Technologies Ion Sequencing Kit v2.0 user's manual. 50 microliters of the sample in the "Enriched-2" tube were transferred to a new 0.2 mL PCR tube. 5 microliters of Control Ion Spheres trade] and 150 microliters of Annealing Buffer™ were added and the solution was mixed and centrifuged for 2 minutes at 15,500×g. Supernatant was removed until only 9 microliters remained. 5 microliters of Sequencing Primer™ were added to the sample and placed on a thermal cycler for a single cycle of 2 minutes at 95° C. and then 2 minutes at 37° C. The sample was then removed from the thermal cycler, mixed with 1 microliter of Sequencing Polymerase™, and incubated at room temperature for 5 minutes.

Meanwhile, a new chip was removed from its packaging and placed in the Ion™ centrifuge adaptor/rotor bucket. Using a Rainin® SR-L200F pipette tip, 50 microliters of 100% isopropanol were added to the large port of the chip and then aspirated from the other port. The chip was washed two times with 50 microliters of Annealing Buffer™ into the large port on the chip which was then aspirated from the other port.

The "Experiment" tab on the main menu of the PGM™ Sequencer was pressed. When prompted, the old chip was replaced with the new one. The barcode scanner was used to scan the chip barcode on the package. After the barcode was entered, the "Chip Check" button was pushed. After Chip Check was complete, the "Next" button was pressed to proceed to chip calibration. Following calibration, the chip was removed, placed back on the Ion centrifuge adaptor/rotor bucket, and washed with 50 microliters of Annealing Buffer into the large port on the chip, which was then aspirated from the other port on the chip. Using the Rainin® Pipette-Lite® LTS-20 pipette with a Rainin® SR-L200F tip, 7 microliters of the sample were deposited to the large port of the chip. The displaced liquid at the other port of the chip was then removed. The Ion Chip™ was then transferred to the centrifuge and spun for 4 minutes. Using a fresh Rainin® SR-L200F tip, the remainder of the sample was deposited to the loading port of the chip. The displaced liquid was removed from the other port and the chip was again centrifuged for 4 minutes. After the final spin was complete, the "Next" button on the PGM screen was pressed and the chip was loaded back onto the Ion Torrent PGM™ machine and the sequencing run started.

Sequence reads were assembled using the DNAStar software SeqmanNexGen® (DNASTAR, Inc., 3801 Regent Street, Madison, Wis. 53705 using the de novo assembly option. Sequence assembly identified seven contigs with greater than 10,000 reads associated each of them. The contigs were trimmed such that they represent the complete open reading frames. The trimmed sequences and corresponding protein sequences are included in the present application as SEQ ID NOs: 4-17. BLASTP analysis of the putative translated open reading frames revealed homology to the seven segments of human influenza C isolates and the isolate was designated C/swine/Oklahoma/1334/2011. The closest homolog for each segment is shown below. The segment noted as encoding the non-structural proteins (NS) is transcribed into mRNA and alternatively spliced to yield two different proteins (NS1 and NS2) as in Table 7 below. The percentage positive represents percent similarity between the isolated influenza C virus and the closest homolog for each segment in the public databases. While PB1 showed moderate homology to the PB1 of the human influenza C isolate C/Johannesburg/1/66 with 85% similarity, all other segments showed lower homology to previously sequenced influenza C, with % similarities for the other segments from 48-71%. The low overall similarity of C/swine/Oklahoma/1334/2011 with previously sequenced viruses demonstrates the uniqueness of this virus.

TABLE 7

| BLAST Homologies | | |
|---|---|---|
| | ORF (amino acids) | Best blast hit (BLASTP) |
| PB2 | 762 | polymerase 2 [Influenza C virus (C/Ann Arbor/1/50)]<br>Identities = 397/762 (52%), Positives = 538/762 (71%), Gaps = 2/762 (0%) |
| PB1 | 720 | polymerase subunit PB1 [Influenza C virus (C/Johannesburg/1/66)]<br>Identities = 512/708 (72%), Positives = 601/708 (85%), Gaps = 2/708 (0%) |
| P3 | 710 | polymerase 3 [Influenza C virus (C/Ann Arbor/1/50)]<br>Identities = 358/722 (50%), Positives = 479/722 (66%), Gaps = 27/722 (4%) |
| HE | 636 | hemagglutinin-esterase [Influenza C virus (C/Catalonia/1318/2009)]<br>Identities = 306/608 (50%), Positives = 399/608 (66%), Gaps = 19/608 (3%) |
| NP | 552 | nucleoprotein [Influenza C virus (C/Ann Arbor/1/50)]<br>Identities = 199/504 (39%), Positives = 297/504 (59%), Gaps = 14/504 (3%) |
| M | 397 | unspliced product of M gene [Influenza C virus (STRAIN C/TAYLOR/1233/47)]<br>Identities = 145/383 (38%), Positives = 221/383 (58%), Gaps = 12/383 (3%) |
| NS1 | 243 | nonstructural protein 1 (NS1) [Influenza C virus (C/Hiroshima/248/2000)]<br>Identities = 76/228 (33%), Positives = 110/228 (48%), Gaps = 21/228 (9%) |
| NS2 | 168 | NS2 [Influenza C virus]<br>Identities = 53/180 (29%), Positives = 87/180 (48%), Gaps = 15/180 (8%) |

Serological Studies to Determine Prevalence

Figure 3:
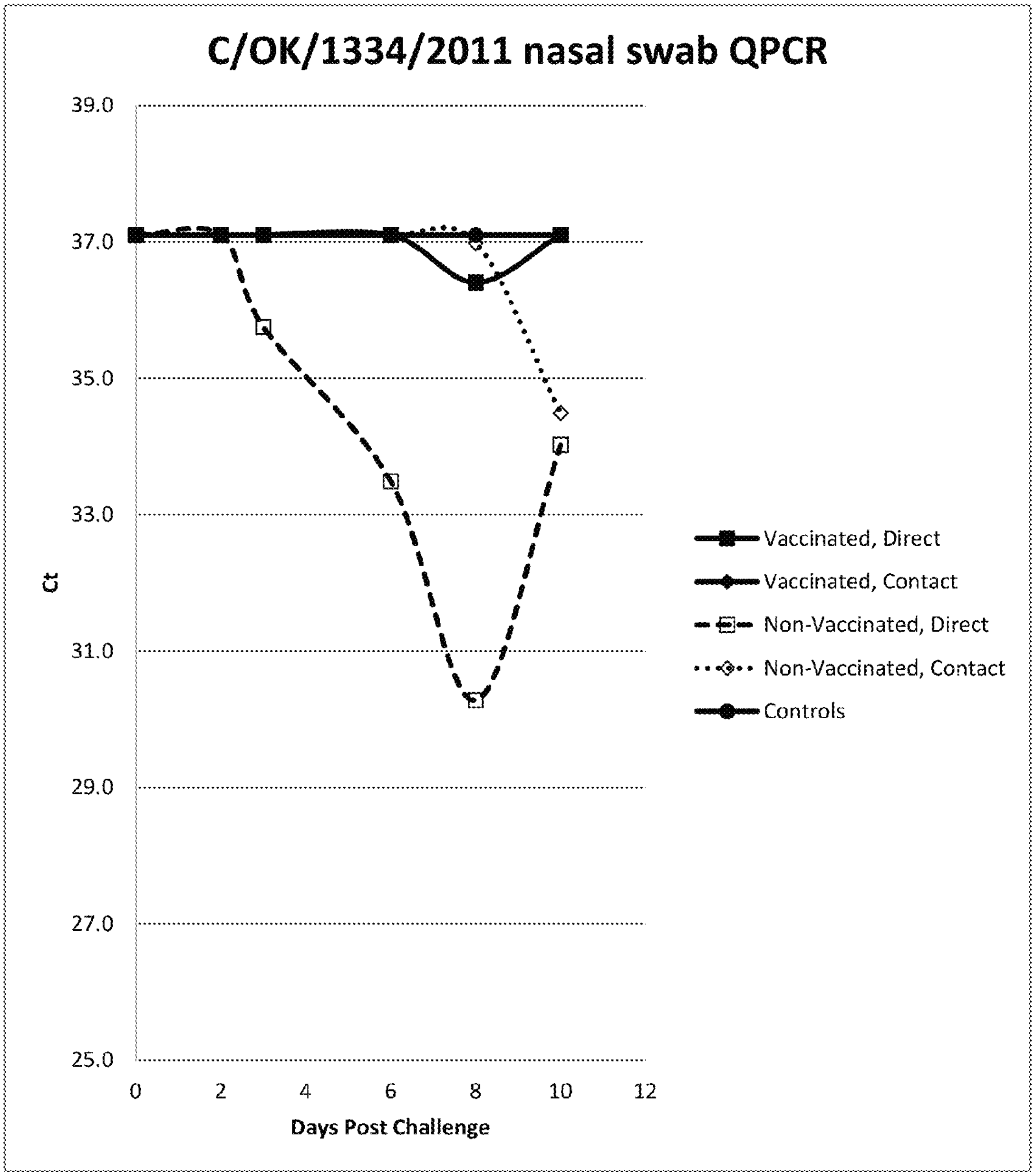
FIG. 3 is a graph showing real-time PCR threshold values in vaccinated and non-vaccinated pigs.

Having established C/swine/Oklahoma/1334/2011 as a novel virus with weak sequence homology to human influenza C, serological studies were performed to determine incidence of infection for both humans and pigs. Approximately 200 random swine sera samples submitted to Newport Laboratories from numerous states were analyzed for antibodies to C/swine/Oklahoma/1334/2011 using the hemagglutination inhibition assay. Approximately 8% of samples were positive in the HI assay with titers from 10-160. Similarly, collaborators at St Jude's Children's Hospital in Memphis, Tenn., performed HI assays on a bank of human sera collected from elderly adults (age 65-95) from Canada. Approximately 28% of the samples had positive HI titers from 10-80. Together, these results demonstrate that both humans and pigs are commonly exposed to C/swine/Oklahoma/1334/2011. These results also suggest that this virus is capable of infecting both humans and pigs Pig Vaccination and Challenge Experiment C/swine/Oklahoma/1334/2011 was grown to a high titer (HA=2560) and inactivated with binary ethyleneimine and then 10% Trigen (an oil in water adjuvant) was added to make a killed virus vaccine. 22 pigs that were serologically negative for antibodies to C/swine/Oklahoma/1334/2011 were vaccinated on days 0 and 14 with 2 mL of inactivated virus vaccine delivered intra muscularly. Serum samples were collected on days 0, 14 and 28 and analyzed for HI titers. 28 pigs were also included as non-vaccinated controls. Vaccinated pigs seroconverted by day 28 with an average HI titer=433. Non-vaccinated pigs were negative on the HI assay. Table 8 and FIG. 3 shows the results. Vaccinated pigs showed strong seroconversion. The rule of thumb for influenza A is that a HI titer>40 is protective. The antibodies measured in pig sera in vaccinated pigs prior to challenge suggests protective antibodies were present. This data is consistent with the challenge results

TABLE 8

HI titers of vaccinated and non-vaccinated pigs

| Vaccinates, Direct Challenge | | | | Vaccinates, Contact Pigs | | | | Non-Vaccinates, Direct Challenge | | | | Non-Vaccinates, Contact Pigs | | | | Controls | | | |
|---|---|---|---|---|---|---|---|---|---|---|---|---|---|---|---|---|---|---|---|
| pig ID | day 14 | day 28 (day 0) | day 42 (day 14) | pig ID | day 14 | day 28 (day 0) | day 42 (day 14) | pig ID | day 14 | day 28 (day 0) | day 42 (day 14) | pig ID | day 14 | day 28 (day 0) | day 42 (day 14) | pig ID | day 0 | day 28 (day 0) | day 42 (day 14) |
| 850 | 40 | 320 | | 856 | 20 | 320 | | 865 | 0 | 0 | | 854 | 0 | 0 | | 851 | 0 | 0 | |
| 852 | 20 | 160 | | 858 | 40 | 640 | | 866 | 0 | 0 | | 857 | 0 | 0 | | 853 | 0 | 0 | |
| 860 | 10 | 320 | | 861 | 0 | 20 | | 870 | 0 | 0 | | 859 | 0 | 0 | | 855 | 0 | 0 | |
| 863 | 10 | 640 | | 864 | 80 | 1280 | | 873 | 0 | 0 | | 867 | 0 | 0 | | 862 | 0 | 0 | 0 |
| 868 | 10 | 80 | | 872 | 20 | 40 | | 874 | 0 | 0 | | 869 | 0 | 0 | | 891 | 0 | 0 | 0 |
| 876 | 0 | 160 | | 875 | 40 | 320 | | 878 | 0 | 0 | | 871 | 0 | 0 | | 896 | 0 | 0 | 0 |
| 880 | 20 | 20 | 640 | 881 | 20 | 1280 | 320 | 883 | 0 | 0 | 20 | 877 | 0 | 0 | 40 | | | | |
| 886 | 80 | 320 | 640 | 882 | 80 | 1280 | 640 | 884 | 0 | 0 | 20 | 879 | 0 | 0 | 40 | | | | |
| 888 | 10 | 640 | 640 | 887 | 10 | 80 | 80 | 889 | 0 | 0 | 40 | 885 | 0 | 0 | 0 | | | | |
| 898 | 80 | 80 | 160 | 890 | 20 | 160 | 160 | 895 | 0 | 0 | 40 | 892 | 0 | 0 | 0 | | | | |
| 899 | 20 | 320 | 320 | 893 | 20 | 640 | 640 | 897 | 0 | 0 | 40 | 894 | 0 | 0 | 0 | | | | |
| Average | 27 | 278 | 480 | | 32 | 551 | 368 | | 0 | 0 | 32 | | 0 | 0 | 16 | | 0 | 0 | 0 |

On day 28, 11 vaccinated and 11 non-vaccinated pigs were challenged intra-nasally with 2 mL of 6.2 log 10 TCID/mL C/swine/Oklahoma/1334/2011. On day 2 post challenge 11 vaccinated and 11 non-vaccinated pigs were added to the room to serve as contact exposure challenge groups. Temperatures were measured every other day from the day of challenge to 14 days post challenge. Table 9 shows the results.

TABLE 9

Pig temperatures following challenge

| pig ID | Day 0 | Day 2 | Day 3 | Day 6 | Day 8 | pig ID | Day 0 | Day 2 | Day 3 | Day 6 | Day 8 |
|---|---|---|---|---|---|---|---|---|---|---|---|
| Vaccinates, Direct Challenge | | | | | | Vaccinates, Contact Pigs | | | | | |
| 850 | 102.5 | 102.1 | 103.4 | 103.6 | | 856 | 104.5 | 102.1 | 104.1 | 104.4 | |
| 852 | 104.3 | 105 | 106.2 | 104.6 | | 858 | 102.9 | 103.3 | 103.6 | 103.1 | |
| 860 | 103.5 | 103.3 | 102.7 | 102.4 | | 861 | 102.9 | 101.8 | 104.2 | 102.7 | |
| 863 | 101.2 | 102.5 | 103 | 102.7 | | 864 | 103.1 | 100 | 103.6 | 102.6 | |
| 868 | 103.1 | 103.9 | 102.2 | 103.6 | | 872 | 102.6 | 103.4 | 103.5 | 102.8 | |
| 876 | 105.7 | 104.5 | 103.2 | 102.8 | | 875 | 102.5 | 102.9 | 103.4 | 103.2 | |
| 880 | 103 | 105.2 | 104.7 | 103.6 | 104.7 | 881 | 103.4 | 103 | 104.7 | 104.3 | 104.1 |
| 886 | 103.8 | 103.9 | 104.7 | 104.1 | 103.8 | 882 | 102.8 | 102.9 | 103.2 | 102.7 | 102.7 |
| 888 | 103.7 | 103.7 | 104.1 | 103 | 103.6 | 887 | 102 | 102.8 | 102.7 | 103.4 | 103 |
| 898 | 101.9 | 103.1 | 104.4 | 103 | 103.3 | 890 | 103.9 | 102.2 | 103.8 | 103.2 | 104.4 |
| 899 | 103.6 | 103.8 | 103.8 | 101.9 | 102.6 | 893 | 104.6 | 102.7 | 103.6 | 103.7 | 103.6 |
| Average | 103.3 | 103.7 | 103.9 | 103.2 | 103.6 | | 103.2 | 102.5 | 103.7 | 103.3 | 103.6 |

TABLE 9-continued

| Pig temperatures following challenge | | | | | | | | | | | |
|---|---|---|---|---|---|---|---|---|---|---|---|
| pig ID | Day 0 | Day 2 | Day 3 | Day 6 | Day 8 | pig ID | Day 0 | Day 2 | Day 3 | Day 6 | Day 8 |
| Non-Vaccinates, Direct Challenge | | | | | | Non-Vaccinates, Contact Pigs | | | | | |
| 865 | 105.1 | 104.6 | 105.2 | 102.7 | | 854 | 104.7 | 103.7 | 104.2 | 102.9 | |
| 866 | 103.4 | 102.7 | 104.4 | 102.1 | | 857 | 103.6 | 103.6 | 103.9 | 103 | |
| 870 | 104.5 | 103.9 | 104 | 103 | | 859 | 102.3 | 103 | 104.3 | 101.9 | |
| 873 | 103.6 | 102.9 | 105.1 | 102.1 | | 867 | 104.2 | 102.8 | 103 | 102.4 | |
| 874 | 104.6 | 103.8 | 105.6 | 101.8 | | 869 | 104.7 | 103.1 | 104.3 | 102.9 | |
| 878 | 102.1 | 102.6 | 102.4 | 103.5 | | 871 | 103.3 | 103.3 | 103.6 | 102.3 | |
| 883 | 103.9 | 104.2 | 104.7 | 104.4 | 104.4 | 877 | 104.2 | 104.1 | 104.8 | 103.2 | 103.3 |
| 884 | 102.5 | 105.3 | 105 | 101.4 | 103.8 | 879 | 103.3 | 102.9 | 100.9 | 100.9 | 103.9 |
| 889 | 103.7 | 104.2 | 104.3 | 103 | 103.1 | 885 | 102.2 | 103.4 | 105.1 | 103.7 | 103.3 |
| 895 | 103.5 | 104.3 | 102.6 | 101.8 | 102.8 | 892 | 104 | 103.9 | 103.8 | 102.8 | 103.6 |
| 897 | 103.1 | 104.8 | 105 | 102.4 | 103 | 894 | 103.8 | 101.6 | 104.1 | 103.1 | 102.3 |
| Average | 103.6 | 103.9 | 104.4 | 102.6 | 103.4 | | 103.7 | 103.2 | 103.8 | 102.6 | 103.3 |
| Controls | | | | | | | | | | | |
| 851 | 103.9 | 104 | 103.3 | 102.6 | | | | | | | |
| 853 | 103.1 | 102.8 | 102.6 | 102.7 | | | | | | | |
| 855 | 103.1 | 103.1 | 103.1 | 103.1 | | | | | | | |
| 862 | 103.7 | 102.8 | 102.7 | 101.8 | 102.3 | | | | | | |
| 891 | 103.6 | 104.3 | 102.7 | 103.1 | 103.1 | | | | | | |
| 896 | 104 | 103.3 | 103.3 | 102.8 | 103.3 | | | | | | |
| Average | 103.6 | 103.4 | 103.0 | 102.7 | 102.9 | | | | | | |

No difference was observed between treatment groups, indicating that the virus does not cause a fever as influenza typically does. Similarly, nasal swabs were collected every other day from the day of challenge to day 14 post challenge.

Method of Assaying the Presence of the Virus

RNA was prepared from the swabs and the presence of influenza C was assayed by reverse transcription real time PCR (rt-RT-PCR) using the following primers and probes designed based on the genome sequence for C/swine/Oklahoma/1334/2011. The nucleotide sequences of the primers and probe is included in the present application as SEQ ID NOs:1-3, wherein Forward Primer=5'-GCT GTT TGC AAG TTG ATG GG-3' (SEQ ID NO:1); Reverse Primer=5'-TGA AAG CAG GTA ACT CCA AGG-3' (SEQ ID NO:2); and the Probe=Cy5-labeled-5'-TTC AGG CAA GCA CCC GTA GGA TT-3'-(SEQ ID NO:3)-IABkQ The results are shown in Table 10 and FIG. 3. "Ct" stands for cycle threshold. In real time PCR, the genetic material (RNA or DNA) is copied by a polymerase by following cycling the sample/enzyme at various temperatures. Real time PCR uses a fluorescent reporter that binds to the produced DNA product. As cycling progresses and DNA product accumulates, more fluorescence is produced. At some point the fluorescence is detected by the PCR machine. A certain level of fluorescence detection is called the threshold. The number of cycles required to generate fluorescence above the threshold level is referred to as the Ct. Real time PCR can quantify the amount of RNA/DNA in the starting sample such that when more DNA/RNA is present prior to PCR, then fewer cycles/doubling will be required to generate fluorescence above the threshold. Consequently, a lower Ct value equates to higher levels of DNA/RNA in the original sample.

TABLE 10

| Real time reverse transcription Ct values for C/swine/Oklahoma/1334/2011 shedding in nasal swabs | | | | | | | | | | | | | |
|---|---|---|---|---|---|---|---|---|---|---|---|---|---|
| pig ID | Day 0 | Day 2 | Day 3 | Day 6 | Day 8 | Day 10 | pig ID | Day 0 | Day 2 | Day 3 | Day 6 | Day 8 | Day 10 |
| Vaccinates, Direct Challenge | | | | | | | Vaccinates, Contact Pigs | | | | | | |
| 850 | 37.1 | 37.1 | 37.1 | 37.1 | | | 856 | 37.1 | 37.1 | 37.1 | 37.1 | | |
| 852 | 37.1 | 37.1 | 37.1 | 37.1 | | | 858 | 37.1 | 37.1 | 37.1 | 37.1 | | |
| 860 | 37.1 | 37.1 | 37.1 | 37.1 | | | 861 | 37.1 | 37.1 | 37.1 | 37.1 | | |
| 863 | 37.1 | 37.1 | 37.1 | 37.1 | | | 864 | 37.1 | 37.1 | 37.1 | 37.1 | | |
| 868 | 37.1 | 37.1 | 37.1 | 37.1 | | | 872 | 37.1 | 37.1 | 37.1 | 37.1 | | |
| 876 | 37.1 | 37.1 | 37.1 | 37.1 | | | 875 | 37.1 | 37.1 | 37.1 | 37.1 | | |
| 880 | 37.1 | 37.1 | 37.1 | 37.1 | 33.6 | 37.1 | 881 | 37.1 | 37.1 | 37.1 | 37.1 | 37.1 | 37.1 |
| 886 | 37.1 | 37.1 | 37.1 | 37.1 | 37.1 | 37.1 | 882 | 37.1 | 37.1 | 37.1 | 37.1 | 37.1 | 37.1 |
| 888 | 37.1 | 37.1 | 37.1 | 37.1 | 37.1 | 37.1 | 887 | 37.1 | 37.1 | 37.1 | 37.1 | 37.1 | 37.1 |
| 898 | 37.1 | 37.1 | 37.1 | 37.1 | 37.1 | 37.1 | 890 | 37.1 | 37.1 | 37.1 | 37.1 | 37.1 | 37.1 |
| 899 | 37.1 | 37.1 | 37.1 | 37.1 | 37.1 | 37.1 | 893 | 37.1 | 37.1 | 37.1 | 37.1 | 37.1 | 37.1 |
| Average | 37.1 | 37.1 | 37.1 | 37.1 | 36.4 | 37.1 | | 37.1 | 37.1 | 37.1 | 37.1 | 37.1 | 37.1 |
| Non-Vaccinates, Direct Challenge | | | | | | | Non-Vaccinates, Contact Pigs | | | | | | |
| 865 | 37.1 | 37.1 | 34.53 | 37.1 | | | 854 | 37.1 | 37.1 | 37.1 | 37.1 | | |
| 866 | 37.1 | 37.1 | 37.1 | 37.1 | | | 857 | 37.1 | 37.1 | 37.1 | 37.1 | | |
| 870 | 37.1 | 37.1 | 37.1 | 37.1 | | | 859 | 37.1 | 37.1 | 37.1 | 37.1 | | |
| 873 | 37.1 | 37.1 | 37.1 | 37.1 | | | 867 | 37.1 | 37.1 | 37.1 | 37.1 | | |
| 874 | 37.1 | 37.1 | 35.2 | 28.6 | | | 869 | 37.1 | 37.1 | 37.1 | 37.1 | | |
| 878 | 37.1 | 37.1 | 37.1 | 31.32 | | | 871 | 37.1 | 37.1 | 37.1 | 37.1 | | |

TABLE 10-continued

Real time reverse transcription Ct values for C/swine/Oklahoma/1334/2011 shedding in nasal swabs

| pig ID | Day 0 | Day 2 | Day 3 | Day 6 | Day 8 | Day 10 | pig ID | Day 0 | Day 2 | Day 3 | Day 6 | Day 8 | Day 10 |
|---|---|---|---|---|---|---|---|---|---|---|---|---|---|
| 883 | 37.1 | 37.1 | 35.05 | 34.85 | 34.23 | 37.1 | 877 | 37.1 | 37.1 | 37.1 | 37.1 | 37.1 | 34.98 |
| 884 | 37.1 | 37.1 | 37.1 | 29.65 | 24.21 | 29.45 | 879 | 37.1 | 37.1 | 37.1 | 37.1 | 37.1 | 40.52 |
| 889 | 37.1 | 37.1 | 34.69 | 35.54 | 35.85 | 29.37 | 885 | 37.1 | 37.1 | 37.1 | 37.1 | 37.1 | 32.49 |
| 895 | 37.1 | 37.1 | 35.5 | 30.26 | 29 | 37.1 | 892 | 37.1 | 37.1 | 37.1 | 37.1 | 37.1 | 27.35 |
| 897 | 37.1 | 37.1 | 32.8 | 29.76 | 28.11 | 37.1 | 894 | 37.1 | 37.1 | 37.1 | 37.1 | 36.53 | 37.1 |
| Average | 37.1 | 37.1 | 35.8 | 33.5 | 30.3 | 34.0 | | 37.1 | 37.1 | 37.1 | 37.1 | 37.0 | 34.5 |
| | | | Controls | | | | | | | | | | |
| 851 | 37.1 | 37.1 | 37.1 | 37.1 | | | | | | | | | |
| 853 | 37.1 | 37.1 | 37.1 | 37.1 | | | | | | | | | |
| 855 | 37.1 | 37.1 | 37.1 | 37.1 | | | | | | | | | |
| 862 | 37.1 | 37.1 | 37.1 | 37.1 | 37.1 | 37.1 | | | | | | | |
| 891 | 37.1 | 37.1 | 37.1 | 37.1 | 37.1 | 37.1 | | | | | | | |
| 896 | 37.1 | 37.1 | 37.1 | 37.1 | 37.1 | 37.1 | | | | | | | |
| Average | 37.1 | 37.1 | 37.1 | 37.1 | 37.1 | 37.1 | | | | | | | |

The Ct values in the above chart show viral RNA levels in the nasal swabs. 37.1=negative. Any value less than 37.1 is positive for viral RNA (hence viral shedding). This data is also graphed in FIG. 3. The non-vaccinated challenge group viral RNA shedding numbers are significantly different from the vaccinates. We ran a Student's t-test on the data and the non-vaccinates that were directly challenged shed virus at higher levels than all other groups ($P<0.001$). Consequently, the vaccine protected pigs. Virus was only detected in one vaccinated pig following challenge, either direct or by contact exposure. In contrast, non-vaccinated pigs began to shed virus on day 3 post challenge (directly challenged) or on day 6 post exposure (contact challenge). This experiment demonstrates the virus is capable of infecting pigs and can replicate in them and is shed to the environment and contact animals. Additionally, pigs vaccinated with a homologous vaccine are fully protected from infection.

Ferret Challenge

Figure 4:
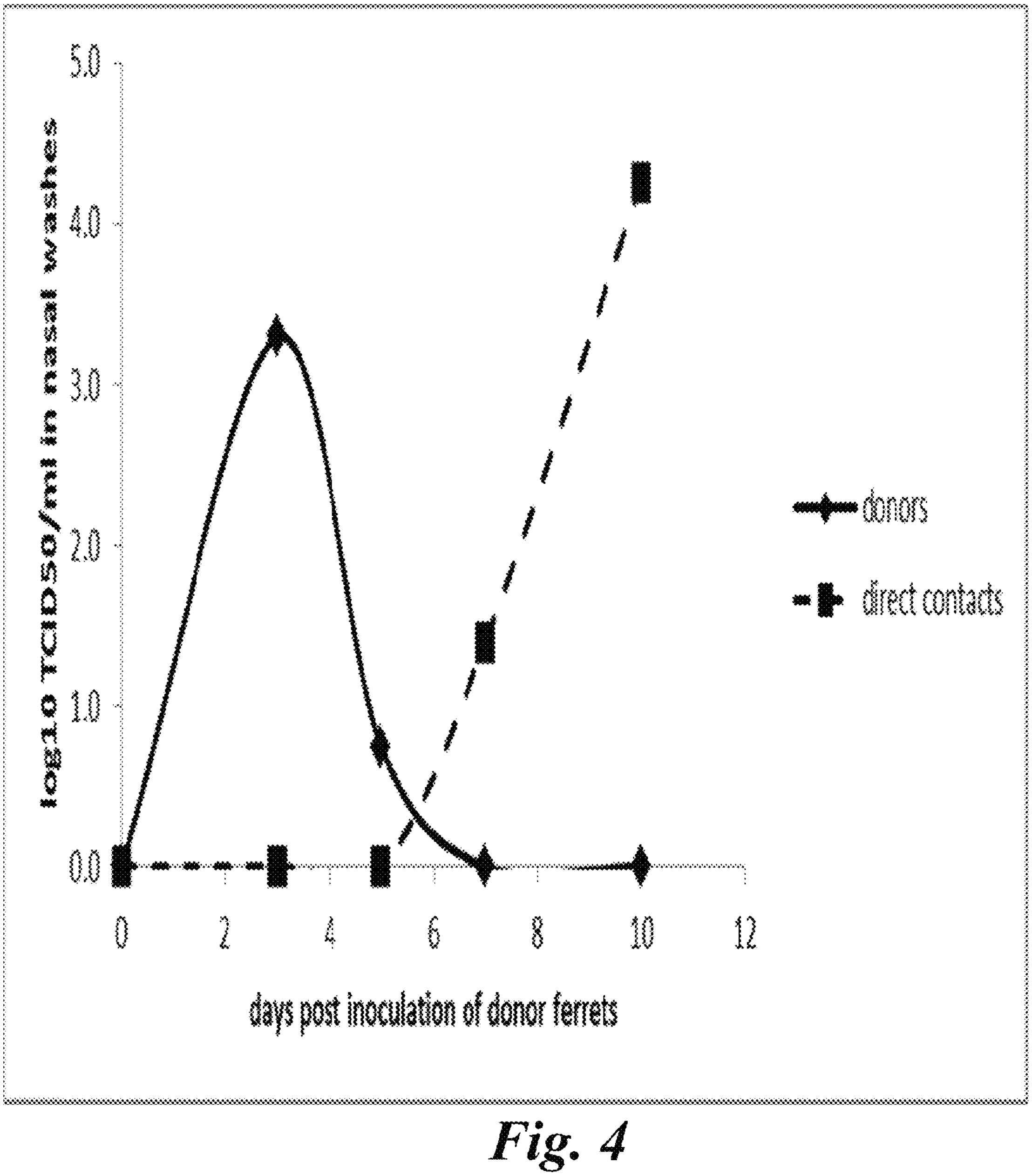
FIG. 4 is a graph showing tissue culture infection dose of ferrets challenged with the virus of the present invention.

Ferrets are commonly used as a surrogate for humans in influenza research as human influenza viruses typically replicate well in ferrets. As influenza C in normally thought of as a human pathogen, C/swine/Oklahoma/1334/2011 was used to challenge ferrets to determine if this virus is a likely human pathogen. Three ferrets were challenged intranasally with 6.0 $\log_{10}$ tissue culture infectious dose 50 per ml ($TCID_{50}$/mL) of C/swine/Oklahoma/1334/2011. On day 1 post challenge, three ferrets were added to the pen to serve as contact animals. Additionally, 3 ferrets were housed in a separate pen to serve as aerosol only exposure animals. Table 11 and FIG. 4 shows the results.

TABLE 11

TCID50/mL of virus detected in nasal swab washes for ferrets infected with C/swine/Oklahoma/1334/2011 by direct inoculation, direct contact or aerosol contact

| ferret id | | days post inoculation (TCID50/mL) 0 | 3 | 5 | 7 | 10 |
|---|---|---|---|---|---|---|
| 55 | direct challenge | | 3.3 | 2.3 | 0.0 | 0.0 |
| 56 | direct challenge | | 3.9 | 0.0 | 0.0 | 0.0 |
| 57 | direct challenge | | 2.8 | 0.0 | 0.0 | 0.0 |
| mean | direct challenge | 0.0 | 3.3 | 0.8 | 0.0 | 0.0 |

TABLE 11-continued

TCID50/mL of virus detected in nasal swab washes for ferrets infected with C/swine/Oklahoma/1334/2011 by direct inoculation, direct contact or aerosol contact

| ferret id | | days post inoculation (TCID50/mL) 0 | 3 | 5 | 7 | 10 |
|---|---|---|---|---|---|---|
| 58 | direct contact | | 0.0 | 0.0 | 2.0 | 4.5 |
| 60 | direct contact | | 0.0 | 0.0 | 0.0 | 4.2 |
| 61 | direct contact | | 0.0 | 0.0 | 2.2 | 4.1 |
| mean | direct contact | 0.0 | 0.0 | 0.0 | 1.4 | 4.3 |
| 62 | aerosol contact | | 0.0 | 0.0 | 0.0 | 0.0 |
| 63 | aerosol contact | | 0.0 | 0.0 | 0.0 | 0.0 |
| 65 | aerosol contact | | 0.0 | 0.0 | 0.0 | 0.0 |
| mean | aerosol contact | | 0.0 | 0.0 | 0.0 | 0.0 |

Virus was detected in nasal swabs by titration of ST cells. Virus was detected by day 3 post challenge in intranasally challenged animals and day 6 post exposure in contact challenge ferrets. No virus was detected in aerosol exposure ferrets. This data demonstrates C/swine/Oklahoma/1334/2011 is capable of infecting ferrets exposed either by direct challenge or contact with challenged animals. However, the virus does not appear to spread via aerosol transmission. This suggests that C/swine/Oklahoma/1334/2011 is likely capable of infecting humans.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A vaccine for protecting a mammal against infection by an influenza C virus, comprising an acceptable carrier, an immunologically effective amount of a binary ethyleneimine-inactivated swine influenza C virus and an oil in water adjuvant; and wherein the virus comprises at least one nucleic acid molecule encoding eight influenza C polypeptides (PB1, PB2, P3, HE, NP, M, NS1 and NS2) having the sequences as set forth in SEQ ID NOs: 5, 7, 9, 11, 13, 15, 17 and 18.

2. The vaccine of claim 1, wherein the isolated strain of influenza C virus was isolated from a pig.

3. The vaccine of claim 2, wherein said isolated strain of influenza C virus is capable of infecting a ferret.

4. The vaccine of claim 2, wherein said vaccine protects pigs against infection by said isolated strain of influenza C virus.

5. The vaccine of claim 1, wherein the oil in water adjuvant is present in an amount of about 10%.

6. The vaccine of claim 1 or 5, wherein the adjuvant is present in an amount of 10%.

7. The vaccine of claim 1, wherein the nucleic acid molecule comprises SEQ ID NO: 4, 6, 8, 10, 12, 14, 16, or combinations thereof.

8. The vaccine of claim 7, wherein the nucleic acid molecule comprises SEQ ID NO: 4.

9. The vaccine of claim 7, wherein the nucleic acid molecule comprises SEQ ID NO: 6.

10. The vaccine of claim 7, wherein the nucleic acid molecule comprises SEQ ID NO: 8.

11. The vaccine of claim 7, wherein the nucleic acid molecule comprises SEQ ID NO: 10.

12. The vaccine of claim 7, wherein the nucleic acid molecule comprises SEQ ID NO: 12.

13. The vaccine of claim 7, wherein the nucleic acid molecule comprises SEQ ID NO: 14.

14. The vaccine of claim 7, wherein the nucleic acid molecule comprises SEQ ID NO: 16.

* * * * *